United States Patent
Zhu et al.

(10) Patent No.: US 6,361,672 B1
(45) Date of Patent: Mar. 26, 2002

(54) MULTIPLE LASER DIODE ELECTROMAGNETIC RADIATION SOURCE IN MULTIPLE ELECTROPHORESIS CHANNEL SYSTEMS

(75) Inventors: Jianzhong Zhu; Robert C. Fry, both of Omaha, NE (US); Arthur P. D'Silva, Ames, IA (US)

(73) Assignee: Transgenomic, Inc., San Jose, CA (US)

( * ) Notice: Subject to any disclaimer, the term of this patent is extended or adjusted under 35 U.S.C. 154(b) by 0 days.

(21) Appl. No.: 09/350,741

(22) Filed: Jul. 9, 1999

Related U.S. Application Data

(63) Continuation-in-part of application No. 09/107,825, filed on Jun. 30, 1998, now abandoned, and a continuation-in-part of application No. 09/107,830, filed on Jun. 30, 1998, now Pat. No. 6,008,055, which is a continuation-in-part of application No. 08/662,467, filed on Jun. 10, 1996, now Pat. No. 5,763,277.

(51) Int. Cl.⁷ .................. G01N 27/26; G01N 27/447
(52) U.S. Cl. .................. 204/603; 204/452; 356/344
(58) Field of Search .................. 204/452, 603; 356/344

(56) References Cited

U.S. PATENT DOCUMENTS

| 6,008,055 A | * 12/1999 | Zhu et al. ............ 356/344 X |
| 6,014,213 A | * 1/2000 | Waterhouse ............ 356/344 |
| 6,084,667 A | * 7/2000 | Melman et al. ............ 356/246 |

OTHER PUBLICATIONS

Philip J. Wyatt, "Multiangle Light Scattering Combined with HPLC" LC–GC, vol. 16, No. 2, Feb. 1997.*

* cited by examiner

*Primary Examiner*—Jill Warden
*Assistant Examiner*—John S. Starsiak, Jr.
(74) *Attorney, Agent, or Firm*—William B. Walker

(57) ABSTRACT

The present invention is a multiple channel electrophoresis system which includes a multiple laser diode illumination source. The multiple laser diode illumination source has a plurality of individual laser diodes, each of which is situated so as to provide independent fluorescence inducing illumination to one of the electrophoresis channels in the multiple channel electrophoresis system. The channels in the multiple channel electrophoresis system can be of many embodiments. And use of the present invention system in a multiple angle light scattering mode is also described.

1 Claim, 13 Drawing Sheets

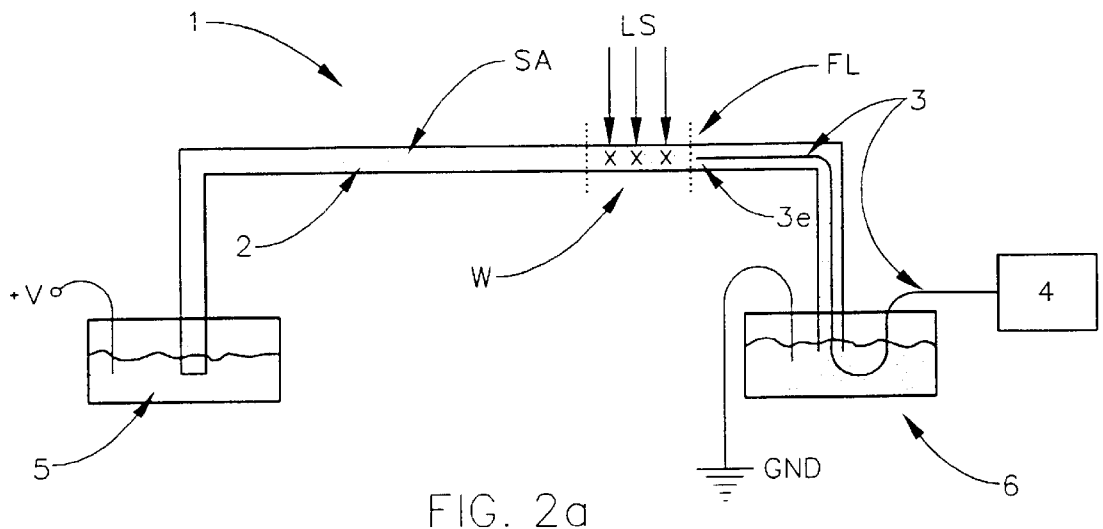
FIG. 2a
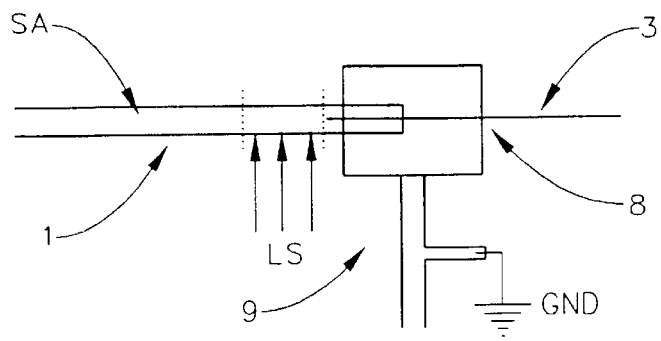
FIG. 2b
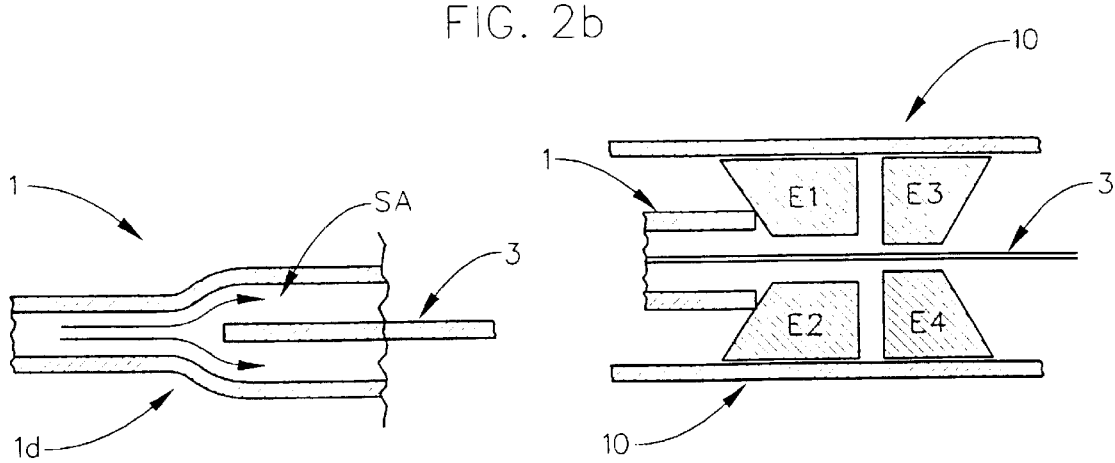
FIG. 3
FIG. 4

MULTIPLE LASER DIODE ELECTROMAGNETIC RADIATION SOURCE IN MULTIPLE ELECTROPHORESIS CHANNEL SYSTEMS

The present Application is a CIP from applications Ser. No. 09/107,825 now abandoned and Ser. No. 09/107,830 now U.S. Pat. No. 6,008,055 both filed Jun. 30, 1998, and which both are CIP's of application Ser. No. 08/662,467 filed Jun. 10, 1996, now U.S. Pat. No. 5,763,277

TECHNICAL AREA

The present invention relates primarily to induced fluorescence, or multiple angle light scattering, mediated identification of sample analytes in solution, and more particularly to a multiple channel electrophoresis system which comprises a multiple laser diode array electromagnetic radiation source, individual laser diodes of which multiple laser diode array electromagnetic radiation source are situated so as to each independently provide a beam of electromagnetic radiation to a specific electrophoresis channel, in said multiple channel electrophoresis system.

BACKGROUND

It is well known to separate different sample analytes present in a solution by electrophoresis, whereby different sample analytes present in a micro-channel, capillary or flow-cell or the like, are caused to migrate at different rates under the influence of an applied electric field. It is also well known to, for instance, analyze fluorescence which is induced by application of electromagnetic excitation energy to sample analytes in a solution present in a micro-channel, capillary or flow-cell, to identify said sample analytes.

Additionally, combination electrophoresis sample separation systems and sample analyte identifying fluorescence inducing systems are known. In fact, a search of Patents has provided a number of relevant references. For instance, two Patents to Yeung et al, U.S. Pat. Nos. 5,498,324 and 5,324,401 describe multiplexed fluorescence detector systems for capillary electrophoresis. Multiplexing is achieved by causing simultaneous application of fluorescence inducing energy from a single laser source to multiple capillaries via a multiplicity of light fibers, each of which light fibers can approach a capillary axially or orthogonally. Another Patent, U.S. Pat. No. 5,584,982 to Dovichi et al., also describes the use of a single laser source, which single laser source simultaneously provides excitation energy to a number of sample containing capillaries. Light fibers are positioned so as to detect the results of said excitation in each capillary and each said light fiber carries excitation energy to an individual detector. U.S. Pat. No. 5,582,705 to Yeung et al, describes a similar system in which a single laser source simultaneously provides excitation energy to a multiplicity of sample analyte containing capillaries present in a multi-channel electrophoresis system. U.S. Pat. No. 5,141,609 to Sweedler et al. is also identified as it describes a CCD array detector system in a capillary electrophoresis system. Additional known Patents are U.S. Pat. Nos. 5,567,294 and 5,439,578 to Dovichi et al.; U.S. Pat. Nos. 5,516,409 and 5,366,608 to Kambara; U.S. Pat. No. 5,413,686 to Klein et al.; U.S. Pat. No. 5,312,535 to Waska et al.; U.S. Pat. No. 5,274,240 to Mathies et al.; U.S. Pat. No. 5,540,825 to Yeung et al.; U.S. Pat. No. 5,585,069 to Zanzucchi et al.; U.S. Pat. No. 5,547,849 to Baer et al.; U.S. Pat. No. 5,356,525 to Goodale et al.; U.S. Pat. No. 5,332,480 to Datta et al.; U.S. Pat. No. 5,239,360 to Moring et al.; U.S. Pat. No. 5,215,883 to Chu; U.S. Pat. No. 4,648,715 to Ford, Jr. et al.; U.S. Pat. No. 5,571,680 to Chen; Japanese Patent No. 4-264859 and WO 89/01620. Additional known Patents which focus on the use of light fibers in electrophoresis systems are Patent to Zare et al., U.S. Pat. No. 4,675,300 describes a method of detecting laser excited fluorescence in an electrokinetic separation system; U.S. Pat. No. 5,140,169 to Evens et al.; U.S. Pat. No. 5,096,671 to Kane et al.; Patent, U.S. Pat. No. 4,837,777 to Jones; Patent to Buckles, U.S. Pat. No. 4,399,099; U.S. Pat. No. 4,740,709 to Leighton et al.; U.S. Pat. No. 4,682,895 to Costello; Another Patent, U.S. Pat. No. 5,068,542, to Ando et al. A known Patent to Zhu, No, U.S. Pat. No. 5,432,096 describes a system and method for identifying sample analyte, (eg. DNA, RNA and Protein etc., based upon electromagnetic radiation absorbtion).

Further disclosed is a paper by Yeung et al, titled "Laser Fluorescence Detector For Capillary Electrophoresis", J. Chromatography, 608(1992), 73–77, describes a laser-based fluorometer for use in detection in capillary electrophoresis. While laser induced fluorescence, in combination with electrophoresis mediated provision of sample analyte into the described system is reported to be a very efficient approach to sample analyte identification, the use of axially oriented optical fibers in a system for detection of sample analyte identifying fluorescence is not described. Said article is incorporated by reference hereinto.

Another known method of identifying analytes in a solution which is caused to be present in a micro-channel, capillary or flow-cell, is that of Multiple-Angle-Light-Scattering (MALS). An article, which describes the technique is titled "Multi-Angle Light Scattering Combined With HPLC", by Wyatt, LC-GC, Vol. 16, No. 2, (Febuary 1997). Briefly, said technique involves impinging light upon a sample analyte containing solution in a flow cell, and intercepting light scattered therefrom with detectors oriented at a number of angular positions. The amount of light intercepted at any angular position is proportional to the product of "Molar Mass and Concentration", and variation in light intercepted at the various angular positions is related to "Molecular Size" of the reflecting molecules. While the theoretical basis of inducing and detecting components in a sample solution utilizing fluorescence is fairly straight forward, (one provides energy to a sample and detects the wavelength of fluorescence emitted), the theoretical basis of multiple-angle light scattering (MALS) requires a bit of elaboration. First, as described in cited article by Wyatt, it is to be understood that the "Excess Rayleigh Ratio" $R(\Theta)$ is defined as the ratio of light intensity at a (MALS) detector positioned at an scattering angular position $(\Theta)$, divided by incident laser intensity $I0$. Next, the relationship between said "Excess Rayleigh Ratio" and the weight average molar mass Mw, and something called the "Second Viral Coefficient) is:

$$K^*c/R(\Theta) \; (1/(Mw \times P(\Theta))+2(A_2 c) \qquad 1$$

where the $P(\Theta)$ is the form factor, which describes the angular variation of the molecular scattering given by:

$$P(\Theta)-1 = \sin^2(\Theta/2) + \sin^4(\Theta/2)- \qquad 2$$

The constant $K^*$ is a function of measured quantities, including the refractive index increment (dn/dc), the refractive index of the solvent $n_0$, and the wavelength of the incident light. The coefficients $\alpha_i$ depend on the structure of the molecule and are usually determined by fitting the collected light-scattering data measured at various concentrations and angles $\Theta_i$, i=1 to N, where N is the total number of angles at which measurements are taken. It is noted that $\Theta_i = 0.0$, $P(\Theta) = 1.0$. The coefficient $\alpha_i$ is always proportional to the molecular mean square radius $(<r_g^2>)$ $$\alpha; \alpha < r_g^2 > = \frac{\sum_i r_i^2 \text{mi}}{\sum_i \text{mi}} = \frac{1}{m}\int r^2 dm$$

where the summation is taken over each mass element $m_i$, and the distances $r_i$ are measured with respect to the molecule's center of mass. It is noted that after separation by chromatography, the concentrations generally are so small that the term involving the solvent-solute interaction $2(A_2c)$ can be ignored. This simplifies Eq. 1. If it is then assumed that the separation is complete and that each chronological "slice" of effluent from a chromatography column contains a unique molar mass, then the polydispersity within the slice and all molar mass moments are equal. Therefore as $(\Theta)$ approaches (0.0), the molar mass may be calculated directly using the extrapolated value $R(\Theta)$ and equation 1, and the mean square radius can be determined by Eq. 2 by using the initial slope of $R(\Theta)$. Again, this description of (MALS) theoretical basis is adapted from the cited Wyatt article, and said Wyatt article is identified and incorporated by reference hereinto as the analysis technique described therein can be practiced in systems which include the present invention multiple laser diode array electromagnetic radiation source, and which system also includes an array of detector means.

Finally, an article which appeared in the Omaha World Herald on Aug. 29, 1997, titled "Microscopic Lab On A Silicon Chip Looms", is identified and disclosed as it describes a system of micro-channels present in a substrate which is fabricated by a photolithographic etching procedure, as developed by Regnier and He at Purdue University. Such "micro-channels" could be utilized as electrophoresis channels in a present invention system.

None of said known references are thought to be particularly relevant to the present invention, however, as none describe the use of a multiple laser diode array source of a plurality of beams of electromagnetic radiation, in a multiple capillary electrophoresis system.

DISCLOSURE OF THE INVENTION

In its most basic sense, the present invention comprises a multi-channel electrophoresis system comprising a laser diode array, where said laser diode array is comprised of a plurality of individual electromagnetic radiation emitting laser diodes. In use, channels in said multi-channel electrophoresis system are typically positioned with respect to said laser diode array so each receives electromagnetic radiation from essentially only one laser diode. Said multi-channel electrophoresis system typically further comprises a multi-element detector system with individual elements therein positioned so as to, in use, typically intercept, electromagnetic radiation, (eg. sample analyte identifying induced fluoresence), from only one multi-channel electrophoresis system channel. (Note that where a multiple angle light scattering (MALS) approach to sample analyte identification is utilized, multiple detector elements in said multi-element detector system can be arranged so as to receive electromagentic radiation from a single electrophoresis system channel).

A present invention multi-channel electrophoresis system can further comprise a focusing lens at at least one location selected from the group consisting of:

between said laser diode array and said multi-channel electrophoresis system; and between said multi-channel electrophoresis system and said multi-element detector system.

One particular arrangement provides a focusing lens at a location between said multi-channel electrophoresis system and said multi-element detector system, and further positions a prism between said focusing lens and said multi-element detector system, wherein said said multi-element detector system is an X-Y array.

It is also noted that fiber optic means can be interposed between each individual diode laser and the channel in said multi-channel electrophoresis system which receives electromagnetic radiation from said individual diode laser.

It is also noted that a detector system can be located so as to receive electromagentic radiation on the same side of the multi-channel electrophoresis system as is present the laser diode array, (ie. in a position which would receive reflected light), or on the opposite side of the multi-channel electrophoresis system, (ie. in a position which would receive transmitted reflected light).

Continuing, while a typical present invention system provides for a laser diode array in combination with a multiple-channel electrophoresis system, wherein said multiple-channel electrophoresis system channels are "micro-channels" in a common substrate, (as commonly utilized in electrophoresis settings), it is also possible to form a multiplicity of electrophoresis system channels from descrete elements. In the following, various electrophoresis system channel providing means are described.

One embodiment of a present invention modular component fiber optic based fluorescence detecting electrophoresis system comprises an electrophoresis channel providing modular axially oriented system component with an axially oriented bore therethrough, and further comprises a fiber optic means, an axially oriented end of said fiber optic means being present within said axially oriented bore. During use, sample analyte fluorescence is caused to occur by the application of energy to sample analyte(s) caused to be present within said axially oriented bore, with said fluorescence inducing energy being entered to said axially oriented bore along a path which is other than essentially parallel to the axial orientation of said axial oriented bore containing modular axially oriented system component. Produced fluorescence enters said axially oriented end of said fiber optic means present within said axially oriented bore, and is transmitted by said fiber optic means to a detector system located distally along said fiber optic means. It is to be appreciated that the fiber optics means can be entered to the axial oriented bore through an open end thereof through which sample analyte is caused to exit, or it can be secured through a closed bore containing wall or end.

Said modular system component with said axially oriented bore therethrough is typically essentially tubular in shape with means for entry of sample analyte, (typically in a solution form), present at ends thereof. In addition, it is noted that said modular axially oriented system component can be entirely transparent to fluorescence producing energy, or only a window in said modular axially oriented system component might be transparent to fluorescence producing energy. In the later case said transparent window is located such that fluorescence producing energy entered therethrough is provided to said axially oriented system near the location of the axially oriented end of said fiber optic means present in said axially oriented bore.

Continuing, a preferred embodiment of the just described modular axially oriented system component further comprises a sample solution containing system source of sample analyte(s) and a sample solution receiving system. In use said modular axially oriented system component bore is caused to be filled with a sample analyte(s) containing sample solution, and sample analyte(s) containing sample solution present at one end of said modular axially oriented system component is caused to be continuous with a sample analyte containing sample solution present in said sample solution containing system source of sample analyte, while sample analyte(s) present at an axially distal end of said modular axially oriented system component is caused to be continuous with sample analyte containing sample solution present in said sample solution receiving system. Said configuration, it will be appreciated is appropriate for use in an electrophoresis scenario wherein an electric potential is applied between said sample analyte containing solution in said sample solution containing system source of sample analyte and a sample solution receiving system, such that sample analyte(s) present therein are caused to migrate through said modular axially oriented system compoent bore.

A method of producing and accessing for analysis, sample analyte identifying fluorescence can involve:
a. providing a modular axially oriented system component as described infra;
b. causing sample analyte(s) to be present in said modular axially oriented system component axially oriented bore;
c. causing sample analyte(s) fluorescence inducing energy to be entered to said modular axially oriented system component axial oriented bore along a path which is other than essentially parallel to the axial orientation of said axial oriented bore;
such that produced fluorescence enters said axially oriented end of said fiber optic means present within said modular axially oriented system component, and is transmitted by said fiber optic means to a detector system located distally along said fiber optic means.

Said described method of producing and accessing for analysis, sample analyte identifying fluorescence, in a preferred embodiment, provides that the step c. act of causing sample analyte(s) fluorescence inducing energy enter said fluorescence inducing energy along a path which is essentially perpendicular to said modular axially oriented system component axial oriented bore orientation.

A more detailed method of producing, and accessing for analysis, sample analyte identifying fluorescence, applicable in an electrophoresis setting, comprises the steps of:
a. providing a modular axially oriented system component as described infra, including said sample solution containing system source of sample analyte(s), and a sample solution receiving system;
b. causing a sample analyte(s) containing sample solution to be continuously present within said modular axially oriented system component axially oriented bore, said sample solution containing system source of sample analyte(s) and said sample solution receiving system;
c. applying an electric potential between sample analyte(s) containing sample solution present in said sample solution containing system source of sample analyte(s) and said sample solution receiving system;
d. causing sample analyte(s) fluorescence inducing energy to be entered to said modular axially oriented system component along a path which is other than essentially parallel to said axial orientation;
such that produced fluorescence enters said axially oriented end of said fiber optic means present within said modular axially oriented system component, and is transmitted by said fiber optic means to a detector system located distally along said fiber optic means.

Again, said described method of producing and accessing for analysis, sample analyte identifying fluorescence, in a preferred embodiment, provides that, the step d. act of causing sample analyte(s) fluorescence inducing energy enter said fluorescence inducing energy along a path which is essentially perpendicular to said modular axially oriented system component axial oriented bore orientation.

While the discussion infra herein describes a utility providing system for producing and accessing sample analyte identifying fluorescence, problems have been encountered in its application. In practice it can be somewhat difficult to thread a fiber optic means through an axially oriented bore, and to maintain a sample analyte flow path in an axial oriented bore when a fiber optic means is threaded therethrough. In addition, it can be very difficult to wash-out such a system between samples. A preferable system was disclosed in priority patent application Ser. No. 08/662,467 filed Jun. 10, 1996, and provides throw-away modular components which can easily be attached and removed from a modular component system for use in inducing and measuring sample analyte identifying fluorescence.

A preferred embodiment of the present invention then comprises a modular component system for use in inducing and measuring sample analyte identifying fluorescence, said modular component system comprising a component with at least four ports. Said modular component system further comprises at least first and second fiber optic means present in, respectively, at least first and second of said at least four ports. During use, sample analyte containing solution is caused to be continuously present in and between said ports thereof which do not have first and second fiber optic means present therein, and sample analyte fluorescence is caused to occur by the application of energy to sample analyte(s) caused to be present within said modular component system. Said fluorescence inducing energy is entered to said modular component system via one of said first and second fiber optic means, such that produced fluorescence enters the remaining said second and first fiber optic means, respectively, and is transmitted by said remaining second or first fiber optic means to a detector system located distally along said remaining second or first fiber optic means, respectively.

One preferred embodiment of the modular component system modular component with at least four ports provides that said at least four ports be oriented in an essentially cross shape, with means for entry and exit of sample analyte present at two ports thereof. In said embodiment, preferably, all present ports are present in a common plane. As well, it is preferred, but not required, that each of said four ports projects at an essentially ninety degree angle with respect to each of the other of said at least four ports.

Another preferred embodiment of the modular component system modular component with at least four ports provides three of said ports in an essentially "tee" shape, with a forth port projecting out of a plane formed by said essentially "tee" shape forming three ports. In this embodiment, preferably, but not necessarily, said forth port projects essentially perpendicularly to the plane formed by said three "Tee" shape forming ports which preferably form a common plane. Again, it is preferred that each of said four ports projects at an essentially ninety degree angle with respect to each of the other of said at least four ports.

As described infra herein with respect to the previously reported axial bore system, the present invention modular component system for use in. inducing and measuring sample analyte identifying fluorescence further comprises a sample solution containing system source of sample analyte (s) and a sample solution receiving system. In use said modular component system component with at least four ports is caused to be filled with a sample analyte(s) containing sample solution, and such that sample analyte(s) containing sample solution present at said source of sample analyte(s) is caused to be continuous with a sample analyte containing sample solution present in said sample solution receiving system. Said continuity being via ports which do not have first and second fiber optic means present therein. Again, in use an electric potential is applied between said sample analyte containing solution in said sample solution containing system source of sample analyte and a sample solution receiving system, such that sample analyte(s) present therein are caused to migrate through said modular component system.

A method of producing and accessing for analysis, sample analyte identifying fluorescence utilizing the present invention modular component system then comprises the steps of:
a. providing a modular component system for use in inducing and measuring sample analyte identifying fluorescence as described infra herein;
b. causing sample analyte(s) to be continuously present in said modular component system component with at least four ports, between ports thereof which do not have fiber optic means present therein;
c. causing sample analyte(s) fluorescence inducing energy to be entered to said modular component system component with at least four ports via one of said first and second fiber optic means;
such that produced fluorescence enters said modular component system component with at least four ports fiber optic means present within one of said second and first ports respectively, and is transmitted by said fiber optic means to a detector system located distally along said fiber optic means.

A more detailed method of producing, and accessing for analysis, sample analyte identifying fluorescence, applicable in an electrophoresis setting, comprises the steps of:
a. providing a present invention modular component system as described infra, including said sample solution containing system source of sample analyte(s), and a sample solution receiving system;
b. causing sample analyte(s) to be continuously present in said modular component system component with at least four ports, between ports thereof which do not have fiber optic means present therein;
c. applying an electric potential between sample analyte(s) containing sample solution present in said sample solution containing system source of sample analyte(s) and said sample solution receiving system;
d. causing sample analyte(s) fluorescence inducing energy to be entered to said modular component system component with at least four ports via one of said first and second fiber optic means;
such that produced fluorescence enters said modular component system component with at least four ports fiber optic means present within one of said second and first ports respectively, and is transmitted by said fiber optic means to a detector system located distally along said fiber optic means.

It is noted that all ports in the modular component systems just described enter into a common internal volume so that sample analyte present contacts the ends of said first and second fiber optic optic means.

Another modular component system for use in inducing and measuring sample analyte identifying fluorescence is comprised of a modular component which comprises an essentially tubular shaped element with an outer wall, one end of said essentially tubular shaped element being open and another end thereof being closed. Said closed end has a fiber optic means for carrying induced fluorescence to a detector system secured therewithin through a securing interface means, such that said fiber optic means for carrying induced fluorescence to a detector system projects from outside said essentially tubular shaped element into said essentially tubular shaped element with an annular space being formed inside said essentially tubular shaped element and around said fiber optic means for carrying induced fluorescence to a detector system. Said annular space formed around said fiber optic means for carrying induced fluorescence to a detector system is accessed at a location between said open end and said closed end of said essentially tubular shaped element by an annular space accessing means which projects through said outer wall of said essentially tubular shaped element. (Note that where said fiber optic means for carrying induced fluorescence to a detector does not actually project beyond the location at which the annular space accessing means which projects through said outer wall of said essentially tubular shaped element, the space accessed is still to be considered as within the scope of the terminology "annular space formed around said fiber optic means for carrying induced fluorescence to a detector system" as the space directly accessed is continuous with said annular space. The terminology "annular space" is further to be considered to include space formed inside an essentially tubular shaped element even in the case where the fiber optic means for carrying induced fluorescence to a detector is caused to be flush with the closed end of the essentially tubular shaped element, or even where the fiber optic means for carrying induced fluorescence to a detector is recessed into said closed end). Continuing, said modular component system further comprises an essentially transparent essentially tubular connection means comprising an essentially transparent tubular wall, said open end of said essentially tubular shaped element being, during use, connected to a source of sample analyte containing solution by way of said essentially transparent essentially tubular connection means. During use, sample analyte(s) containing solution is caused to be continuously present in said essentially transparent essentially tubular connection means, in said annular space inside said essentially tubular shaped element and around said fiber optic means for carrying induced fluorescence to a detector system, and in said annular space accessing means, while sample analyte fluorescence is caused to occur by the application of energy to sample analyte(s) in said sample analyte(s) containing solution present within said essentially transparent essentially tubular connection means. Said fluorescence inducing energy is entered through the essentially transparent tubular wall of said essentially transparent essentially tubular connection means along a pathway oriented other than parallel to the orientation of said fiber optic means for carrying induced fluorescence to a detector system present in said essentially tubular shaped element, with said produced fluorescence being caused to be transmitted to a detector system located distally along said fiber optic means outside said essentially tubular shaped element, by said fiber optic means for carrying induced fluorescence to a detector system.

The presently described modular component system for use in inducing and measuring sample analyte identifying fluorescence typically further comprises a sample solution containing system source of sample analyte(s) and a sample solution receiving system. In use sample analyte(s) containing sample solution present at said source of sample analyte(s) is caused to be continuous with a sample analyte containing sample solution present in said sample solution receiving system. In use an electric potential is applied between said sample analyte containing solution in said sample solution containing system source of sample analyte and said sample solution present in said sample solution receiving system, with the result being that sample analyte (s) are caused to migrate through said modular component system essentially tubular shaped element under the presence of a resulting electric field.

A method of producing and accessing for analysis, sample analyte identifying fluorescence comprises the steps of:
a. providing a modular component system for use in inducing and measuring sample analyte identifying fluorescence as just described.
b. causing sample analyte(s) to be continuously present in said modular component system essentially tubular shaped element and essentially transparent essentially tubular connection means;
c. causing sample analyte(s) fluorescence inducing energy to be entered to through said essentially transparent wall of said essentially transparent essentially tubular connection means;

such that produced fluorescence enters said fiber optic means and is transmitted by said fiber optic means to a detector system located distally along said fiber optic means.

A preferred embodiment provides that fluorescence inducing energy is caused to be entered through an essentially transparent wall of said essentially transparent essentially tubular connection means, however, it is within the scope of the present invention to provide a fluorescence inducing energy "transparent" window region in said modular component system, or to fabricate the entire modular component system from such material and then enter said fluorescence inducing energy directly therethrough.

A more detailed method of producing and accessing for analysis, sample analyte identifying fluorescence comprising the steps of:
a. providing a modular component system for use in inducing and measuring sample analyte identifying fluorescence as just described.
b. causing sample analyte(s) to be continuously present in said modular component system essentially tubular shaped element and essentially transparent essentially tubular connection means;
c. applying an electric potential between sample analyte(s) containing sample solution present in said sample solution containing system source of sample analyte(s) and said sample solution receiving system;
d. causing sample analyte(s) fluorescence inducing energy to be entered through said essentially transparent wall of said essentially transparent essentially tubular connection means;

such that produced fluorescence enters said fiber optic means and is transmitted by said fiber optic means to a detector system located distally along said fiber optic means.

Again, a preferred embodiment provides that fluorescence inducing energy is caused to be entered through an essentially transparent wall of said essentially transparent essentially tubular connection means, however, it Is within the scope of the present invention to provide a fluorescence inducing energy "transparent" window region in said essentially tubular shaped element modular component or to fabricate the entire essentially tubular shaped element modular component from such material and then enter said fluorescence inducing energy directly therethrough.

A multiple angle light scattering (MALS) approach to sample analyte identification can be practiced with any of the above systems where a beam of electromagentic radiation can be caused to impinge upon a solution which contains sample analyte. In that light, it is to be understood that a method of producing and accessing a multiplicity of signals for analysis can comprise the steps of:
a. providing a multi-channel electrophoresis system comprising multiple electrophoresis channels and a laser diode array for use in inducing sample analyte identifying fluorescence, said laser diode array being comprised of a plurality of individual diode lasers, said channels in said multi-channel electrophoresis system being positioned with respect to said laser diode array so that, in use, at least one of said channels can receive electromagnetic radiation emitted from essentially only one individual laser diode; which multi-channel electrophoresis system includes at least one channel which is a modular component system for use in inducing and measuring sample analyte identifying fluorescence, said multi-channel electrophoresis system being for use in evaluating parameters which characterize selections from the group consisting of:

the presence of, the molar mass of, the concentration of, the product of molar mass and concentration representing parameter values, and the molecular size of present sample analyte; said multi-channel electrophoresis system further comprising a system for practicing multiple angle light scattering detection, said system for practicing multiple angle light scattering detection comprising as a source of a beam of electromagnetic radiation, an individual laser diode in said laser diode array, means for causing a beam of electromagnetic radiation provided by said individual laser diode to impinge upon a sample solution which contains sample analyte(s), and a multiplicity of detector means, each oriented at one of a multiplicity of angles as measured from a perpendicular to the sample solution at the point at which said means for causing said beam of electromagnetic radiation to impinge upon a sample solution causes, in use, a beam of electromagnetic radiation to impinge upon said sample solution;

b. causing a sample analyte containing solution to migrate through said multi-channel electrophoresis system by electrophoresis;
c. causing a beam of electromagnetic radiation to impinge upon a sample solution;
d. obtaining signals from at least two of said multiplicity of detector means; and
e. performing analysis of said at least two of said multiplicity of detector means to evaluate parameters which characterize selections from the group consisting of: (the presence of, the molar mass of, the concentration of, the product of molar mass and concentration representing parameter values, and the molecular size of present sample analyte(s)).

The present invention system will be better understood by reference to the Detailed Description Section of this Disclosure, with reference being had to the accompanying Drawings.

SUMMARY OF THE INVENTION

It is a primary purpose of the present invention to teach use of a laser diode array in a multi-channel electrophoresis system for inducing sample analyte(s) fluorescence.

It is another purpose of the present invention to provide modular component systems and methods of use thereof, for inducing and detecting sample analyte(s) identifying fluorescence.

It is a yet another purpose of the present invention to disclose a system which includes a fiber optic means, and is a modular component system in which sample analyte fluorescence is caused to occur, by the application of energy to present sample analyte(s) is disclosed.

It is still yet another particular purpose of the present invention to disclose that sample analyte(s) fluorescence inducing energy can be entered and exited from a system of the present invention via fiber optic means.

It is yet still another purpose of the present invention to describe modular component systems which allows for easy sample change by change of a disposable modular component.

It is another purpose of the present invention to describe the use of multiple laser diode arrays and modular component systems in systems for practicing multiple angle light scattering.

BRIEF DESCRIPTION OF THE DRAWINGS

FIG. 2a shows an axially oriented system, including an axially oriented fiber optic means.

FIG. 2b shows an axially oriented optical fiber means axially entered to an oriented system, via a sealed or sealable means.

FIG. 3 shows an shows an axially oriented system, including an axially oriented fiber optic means, in which the inner diameter of the axially oriented system is increased at the location of contained axially oriented fiber optic means.

FIG. 4 shows an alignment system means by which the axially oriented system and the fiber optic means can be easily aligned in use.

FIGS. 9a1, 9a2, 9b and 9c show another preferred embodiment of a present invention modular component system component with at least four ports.

DETAILED DESCRIPTION

Figure 1A:
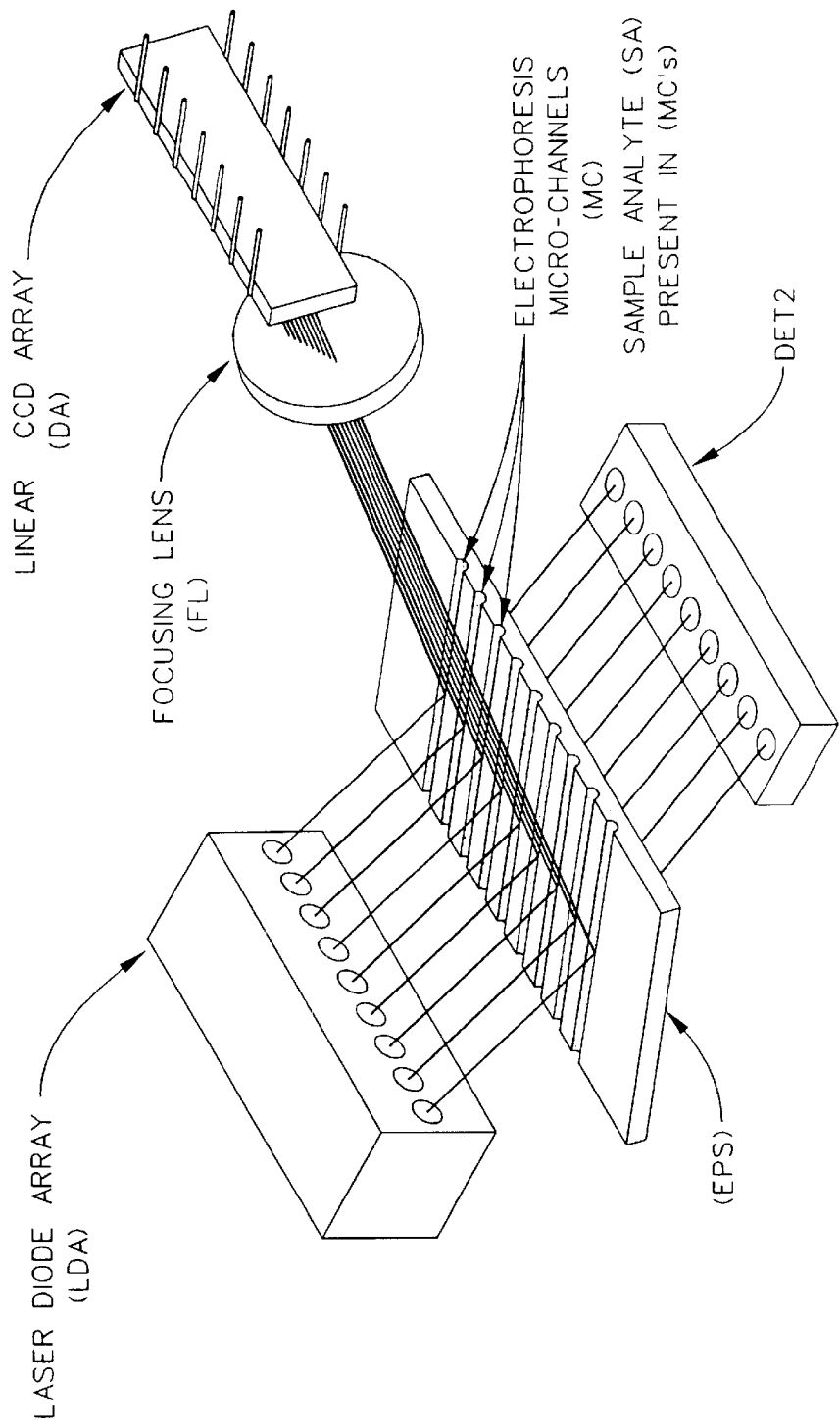
FIG. 1a shows a laser diode array in present invention combination with an electrophoresis micro-channel system, a focusing lens and a linear CCD array.
Figure 1B:
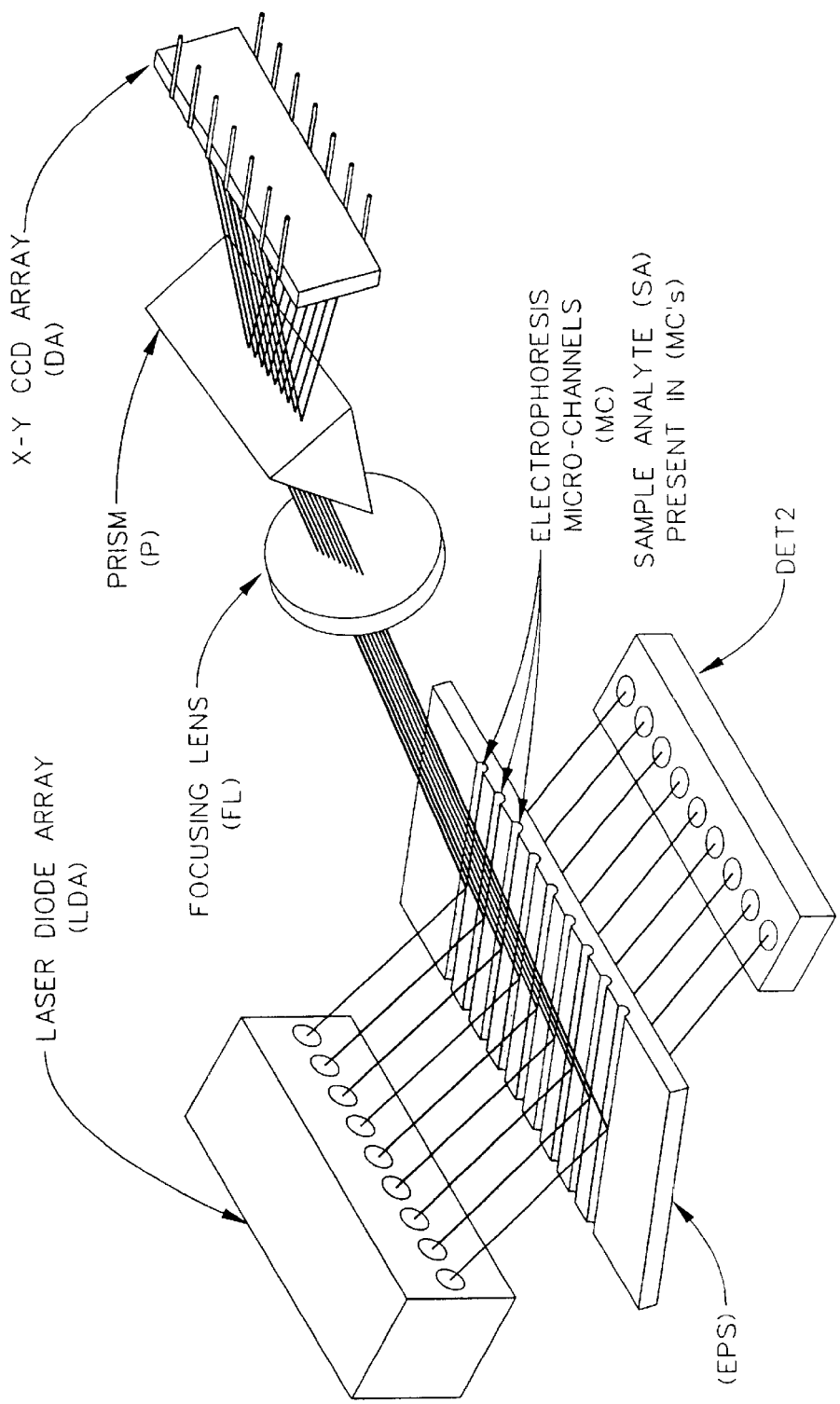
FIG. 1b shows a laser diode array in present invention combination with an electrophoresis micro-channel system, a focusing lens, a prism and an X-Y CCD array.
Figure 1C:
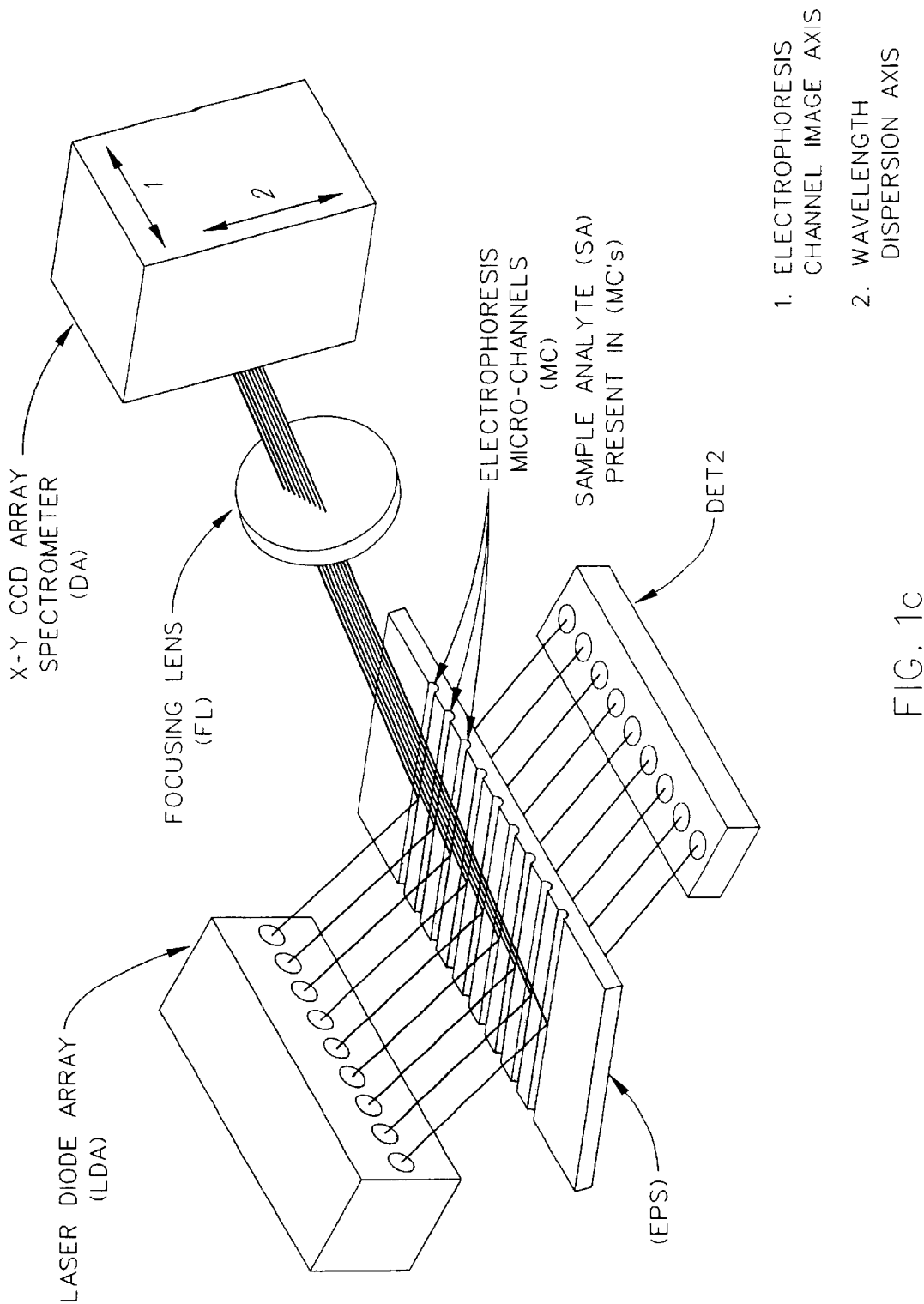
FIG. 1c shows a laser diode array in present invention combination with an electrophoresis micro-channel system, a focusing lens and an X-Y CCD array spectrometer.
Figure 1D:
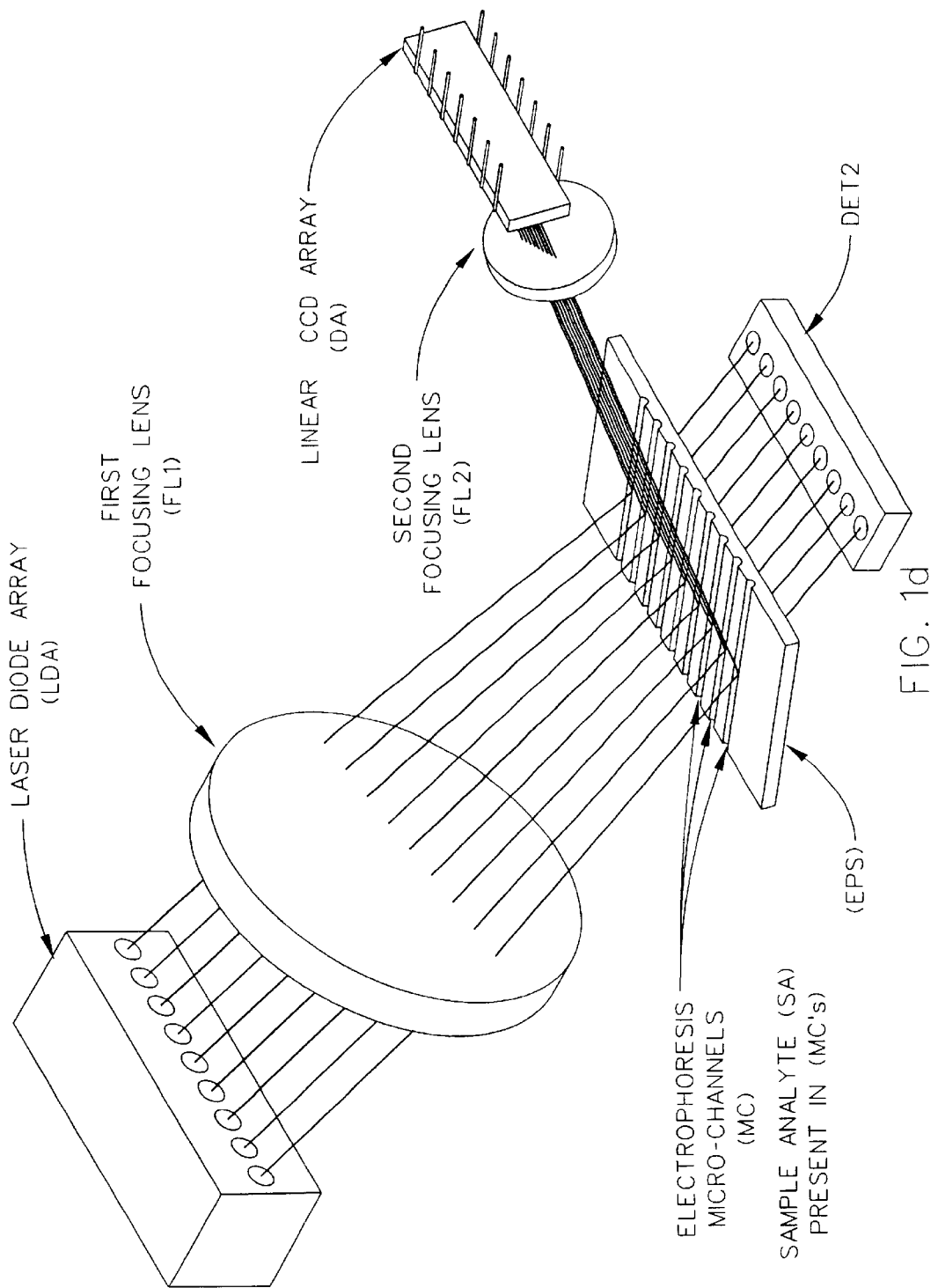
FIG. 1d shows a laser diode array in present invention combination with, sequentially, a first focusing lens, an electrophoresis micro-channel system, a second focusing lens and a linear CCD array.
Figure 1E:
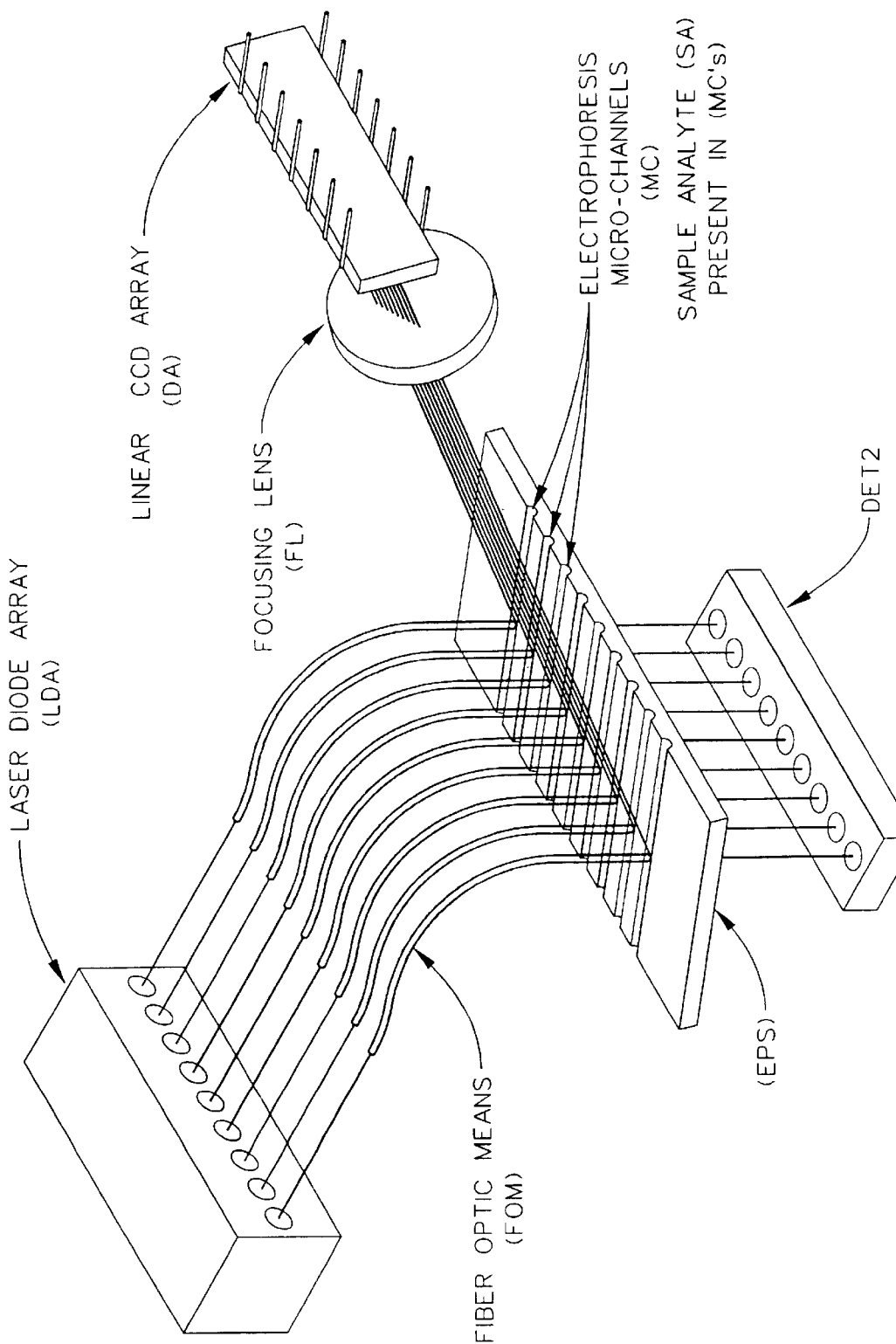
FIG. 1e shows the system of FIG. 1a with fiber optic means added between laser diodes of said laser diode array and the electrophoresis micro-channel system channels.
Figure 1F:
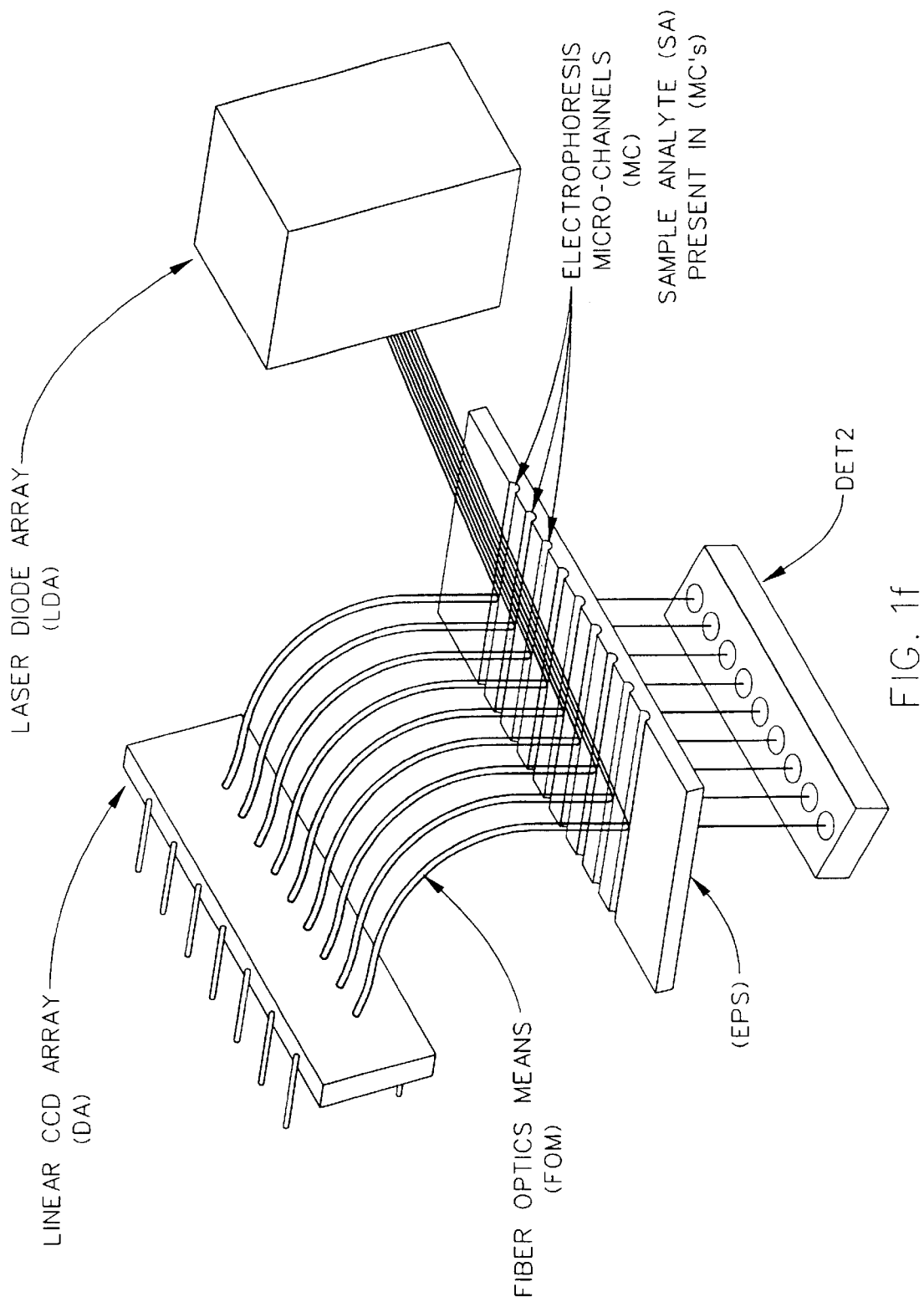
FIG. 1f shows the system of FIG. 1a with fiber optic means added between the electrophoresis micro-channel system channels and the linear CCD array.

Turning now to the Drawings, the basic system of the present invention is shown in FIGS. 1a–1f. FIGS. 1a–1f show that the present invention is a primarily multi-channel electrophoresis system (EPS) comprising a "Laser Diode Array" (LDA), where said laser diode array (LDA) is comprised of a plurality of "Individual Diode Lasers", (demonstrated as a plurality of circles inside the block labeled "Laser Diode Array" (LDA) in each of said FIGS. 1a–1e). As shown, in use, each channel (labeled "Micro-Channels" (MC)), in said multi-channel electrophoresis system (EPS) is positioned with respect to said laser diode array (LDA) so that it receives electromagnetic radiation from, preferably, only one laser diode therein. Said multi-channel electrophoresis system (EPS) further comprises a multi-element detector system (DA) with individual elements therein positioned so as to, in use, typically intercept electromagnetic radiation from only one multi-channel electrophoresis system (EPS) channel (MC). (Note that where a multiple-angle light scattering (MALS) procedure is pursued multiple detector elements in said multi-element detector system (DA) can be arranged so as to receive electromagnetic radiation from a single electrophoresis system channel). A present invention multi-channel electrophoresis system can further comprise a "Focusing Lens" (FL), (FL1), (FL2) at a location selected from the group consisting of: (between said laser diode array (LDA) and said multi-channel electrophoresis system (EPS), (see for instance, (FL1) in FIG. 1d), and between said multi-channel electrophoresis system (EPS) and said multi-element detector system (DA), (see (FL) in FIGS. 1a, 1b, and 1c, and (FL2) in FIG. 1d). As shown in FIG. 1b, one particular arrangement provides a focusing lens (FL) at a location between said multi-channel electrophoresis system (EPS) and said multi-element detector system (DA), and further positions a prism (P) between said focusing lens (FL) and said multi-element detector system (DA), wherein said multi-element detector system (DA) is an X-Y array. Additionally, as shown by FIGS. 1e and 1f, fiber optic means (FOM) can be interposed between each individual diode laser in said laser diode array (LDA) and the channel in said multi-channel electrophoresis system (EPS) which receives electromagnetic radiation from said individual diode laser, and/or between each channel in said multi-channel electrophoresis system (EPS) and individual detector elements in said multi-element detector system (DA). It should also be noted that electromagnetic radiation is shown passing through the electrophoresis channels (MC) in FIGS. 1a–1f, and while not shown in detail, it is possible to monitor said transmitted electromagnetic radiation an determine absorbence properties of a sample analyte (SA) present in said micro channels (MC), or fluorescence which radiates downward to the element identified as detector two (DET2).

In more detail, FIG. 1a shows a laser diode array (LDA) in present invention combination with an electrophoresis micro-channel system (EPS), a focusing lens (FL) and a linear CCD array (DA). (It is noted that a preferred, but not limiting, multi-element detector system is a Charge Coupled Device (CCD) array). Focal length and placement of the focusing lens (FL) can be adjusted to alter the magnification ratio thereof so that the electromagnetic energy entering thereto after interaction with sample analyte in the electrophoresis micro-channels (MC), is properly formatted to functionally enter the shown CCD array (DA). FIG. 1b shows a laser diode array (LDA) in present invention combination with an electrophoresis micro-channel system (EPS), a focusing lens (FL), a prism (P) and an X-Y CCD array (DA). The purpose of the prism (P) is to separate multiple fluorescence wavelengths from one another. For example, two fluorescent tags might be might be added to sample analyte (S) present in electrophoresis microchannels, which tags identify the presence of two different molecules. FIG. 1c shows a laser diode array (LDA) in present invention combination with an electrophoresis micro-channel system (EPS), a focusing lens (FL) and an X-Y CCD array spectrometer (DA). This system is similar to that shown in FIG. 1b, but the prism (P) is replaced with an X-Y CCD array spectrometer (DA). The X-Y CCD array spectrometer (DA) can be a complete stigmatic grating spectrometer with CCD detector elements in the focal plane thereof. Electrophoresis channels are focused along a "long" axis of the spectrometer entrance slit. Multiple fluroescence spectra are "stacked" along a perpendicular axis. Any number of fluorescent tags can thereby be temporarily monitored. FIG. 1d shows a laser diode array (LDA) in present invention combination with, sequentially, a first focusing lens (FL1), an electrophoresis micro-channel system (EPS), a second focusing lens (F2) and a linear CCD array (DA). The first focusing lens (FL1) serves to adjust the size of the laser diode array (LDA) image so that it matches electrophoresis channel spacing. FIG. 1e shows the system of FIG. 1a with fiber optic means (FOM) added between laser diodes of said laser diode array (LDA) and the electrophoresis microchannel system (EPS) channels. FIG. 1f shows the system of FIG. 1a with fiber optic means (FOM) added between the electrophoresis micro-channel system (MC) channels and the linear CCD array (DA).

The micro-channels identified in FIGS. 1a–1f can comprise tubes, or etched regions in a substrate, (such as can be produced by photolithography and wet or plasma etching), and said etched regions can be capped with an essentially transparent material to provide an internal space in which sample analyte containing solution can be caused to be present in use. In brief, any micro-channel which can perform the function indicated in FIGS. 1a–1f is to be considered within the scope of the present invention.

Continuing, in the following, specific systems for inducing and detecting sample analyte (SA) identifying fluorescence, (which utilize fiber optics and which can replace the Electrophoresis Micro-Channels shown in FIGS. 1a–1f), are described in detail. It should be kept in mind, however, that the source of electromagnetic radiation which induces sample analyte (SA) identifying fluorescence, or which interacts with sample analyte (SA) in a multiple-angle light scattering (MALS) manner, in any of said specific systems for inducing and detecting sample analyte (SA) identifying fluorescence described infra and supra herein, comprises a laser diode in a laser diode array.

Turning now to FIG. 2a, there is shown a modular axially oriented system for use in inducing and measuring sample analyte (SA) identifying fluorescence (FL). Said modular axially oriented system comprises a modular axially oriented system component with an axially oriented bore (2) therethrough, and further comprises a fiber optic means (3), an axially oriented end (3e) of which fiber optic means (3) is present within said modular axially oriented system component axially oriented bore (2). It should be noted that said fiber optic means (3) is threaded into the axially oriented bore (2) from an open right oriented side thereof, through which sample solution analyte flows in use. While FIG. 2a demonstrates one axially oriented system embodiment, FIG. 2b shows that said axially oriented fiber optic means (3) could be entered through a sealed or sealable opening (8) in a retaining means (9) for said axially oriented system (3), such that said fiber optic means (3) is entered thereto directly in line with said axially oriented system bore (2). Such a configuration is within the scope of the axially oriented system, and is better described with respect to FIGS. 11a–12d.

Referring again to FIG. 2a, during use, sample analyte fluorescence (FL) is caused to occur by the application of energy from source (LS) to sample analyte(s) (SA) which are caused to be present within said axially oriented bore (2), with said fluorescence (FL) inducing energy, from source (LS) being entered to said axially oriented bore (2) along a path which is other than essentially parallel to said axially oriented bore (2) axial orientation. Produced fluorescence (FL) enters said axially oriented end (3e) of said fiber optic means (3) present within said axially oriented bore (2), and is transmitted by said fiber optic means to a detector system (4) located distally along said fiber optic means (3).

The described modular axially oriented system component (1) is typically essentially tubular in shape with means for entry/exit of sample analyte, (SA), typically in a solution form, present at ends thereof. In addition, it is noted that the entire modular axially oriented system component (1) can be transparent to fluorescence (FL) producing energy from source (LS), or only a window (W) in said modular axially oriented system component (1) might be transparent to fluorescence (FL) producing energy from source (LS). In the later case said transparent window (W) is located such that fluorescence (FL) producing energy from source (LS) entered therethrough is provided to said modular axially oriented system component (1) near the location of the axially oriented end (3e) of said fiber optic means (3) present in said axially oriented bore (2).

A preferred embodiment of the described modular axially oriented system further comprises a sample solution containing system source of sample analyte(s) (5) and a sample solution receiving system (6). In use said axially oriented system bore (2) is caused to be filled with a sample analyte (s) (SA) containing sample solution, and sample analyte(s) (SA) containing sample solution present at one end of said axially oriented system (1) is caused to be continuous with a sample analyte containing sample solution present in said sample solution containing system source of sample analyte (5), while sample analyte(s) present at an axially distal end of said axially oriented system is caused to be continuous with sample analyte containing sample solution present in said sample solution receiving system (6). Said configuration, it will be appreciated is appropriate for use in an electrophoresis scenario wherein an electric potential (V+) is applied to said sample analyte containing solution in said sample solution containing system source of sample analyte (5) and a ground potential (GND) is applied to said sample solution receiving system (6), such that sample analyte(s) (SA) present therein are caused to migrate through said axially oriented system bore (2). Sample analytes will be caused to transverse the length of the axially oriented system (1) at rates dependent upon, for instance, charge and mass thereof.

FIG. 3 shows that the modular axially oriented system component (1) can provide an increased inner diameter (1d) at the point at which the fiber optic means (3) enters thereto. Said increased inner diameter (1d) provides a non-constricted annular space in which sample analyte (SA) containing sample solution (5) can flow, in the presence of said fiber optic means (3).

FIG. 4 shows an alignment system means by which the modular axially oriented system component (1) and the fiber optic means (3) can be easily aligned in use. Shown are elements (E1), (E2), (E3) & (E4). Each of said elements presents with an angled surface which in use is caused to face the entry of the axially oriented system (1) or the fiber optic means (3), by position retention mounting in securing means (10). Note that angled surfaces of elements (E1) & (E2) provide centering of an axially oriented system (1) entered thereto, and angled surfaces of elements (E3) & (E4) provide centering means for fiber optic means (3) entered thereto. Note that the centering effect of elements (E3) & (E4) provides the fiber optic means (3) centrally in the modular axially oriented component system (1). That is, the vertically shown length of element (E4) is greater than that of element (E2). In use a user can then easily enter fiber optic means (3) to modular axially oriented system component (1) by simple laterally imposed motion of each, as viewed in FIG. 4.

Note, it is to be understood that terminology "axially oriented system" can mean a capillary tube with an inner "bore" diameter on the order of, for instance, approximately one-hundred (100) microns, and the terminology "fiber optic means" can mean an accompanying electromagnetic wavelength transmitting means with an outer diameter of, for instance, seventy-five (75) microns diameter or less.

With the foregoing disclosure in mind, it should be realized that while the discussion infra herein describes a utility providing system for producing and accessing sample analyte identifying fluorescence, problems have been encountered in its application. In practice it can be difficult to thread a fiber optic means through an axially oriented bore, and to maintain a sample analyte flow path in an axial bore when a fiber optic means is threaded therethrough. In addition, it can be difficult to wash-out such a system between samples. A preferable system would provide "throw-away" modules which can easily be attached and removed from a modular component system for use in inducing and measuring sample analyte identifying fluorescence.

Figure 5:
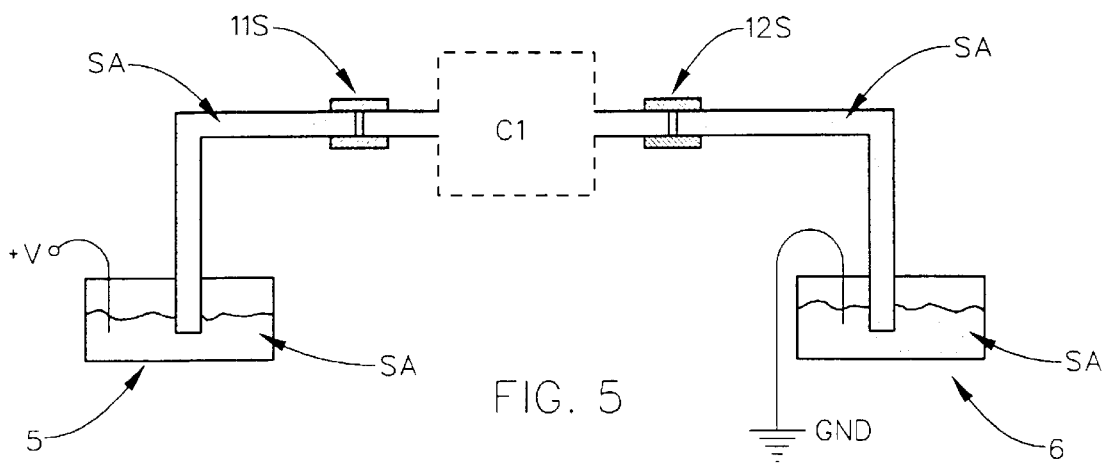
FIG. 5 shows a modular component system of the present invention.
Figure 7:
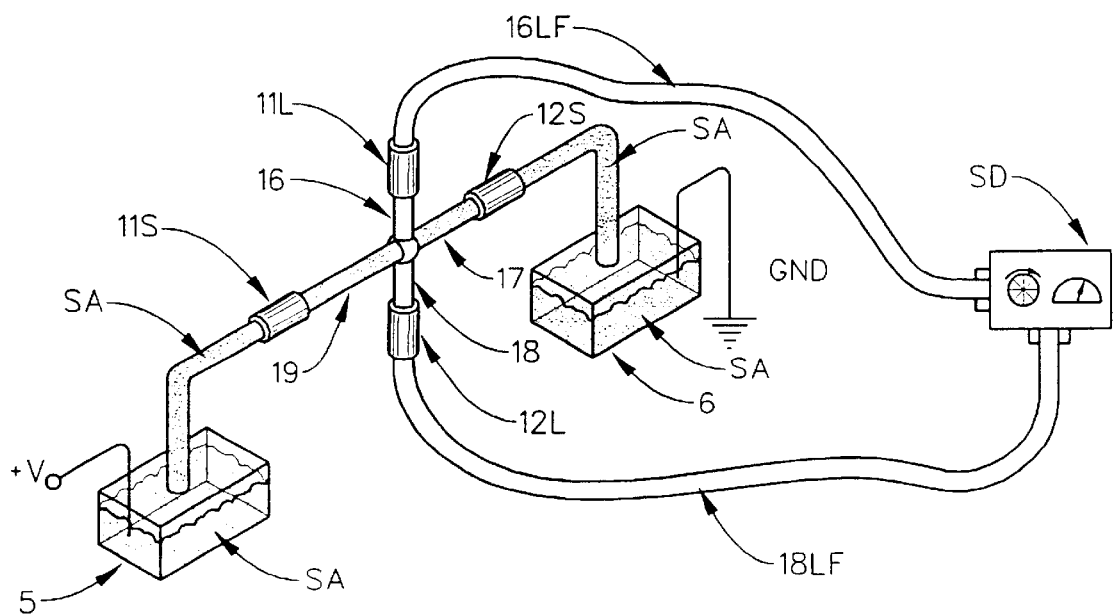
FIG. 7 shows a present invention modular system with the modular component system component of FIGS. 6a, 6b and 6c mounted therein.
Figure 8:
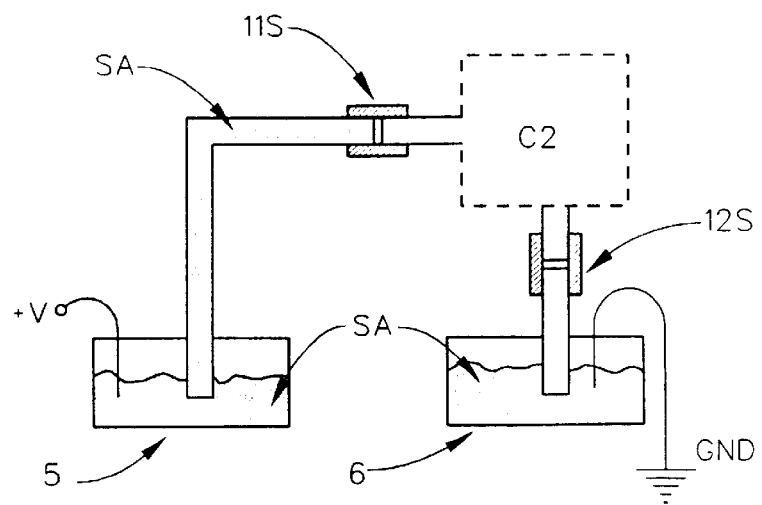
FIG. 8 shows a modular component system of the present invention.

Proceeding, FIGS. 5 and 8 show present invention modular component systems comprised of a source of sample solution containing system source of sample analyte(s) (5) and a sample solution receiving system (6). Shown as coupled to said modular component systems, via connectors (11s) & (12s), are modular component system components identified as (C1) in FIG. 5 and as (C2) in FIG. 8. Said modular component system component (C1) is better shown in FIGS. 6a, 6b, 6c, 6d & 7, while modular component system component (C2) is better shown in FIGS. 9a1, 9a2, 9b, 9c & 10.

Figure 6A:
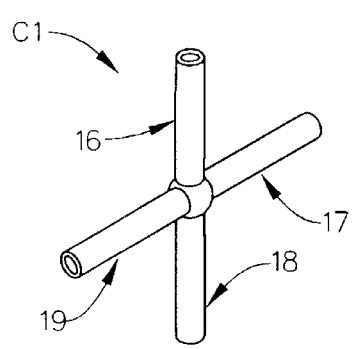
FIGS. 6a, 6b and 6c show one preferred embodiment of a present invention modular component system component with at least four ports with two present fiber optic means placed at one-hundred-eighty degrees with respect to one another.
Figure 6B:
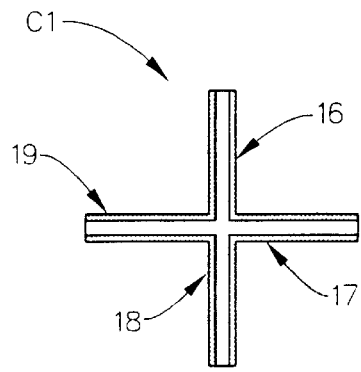
Figure 6C:
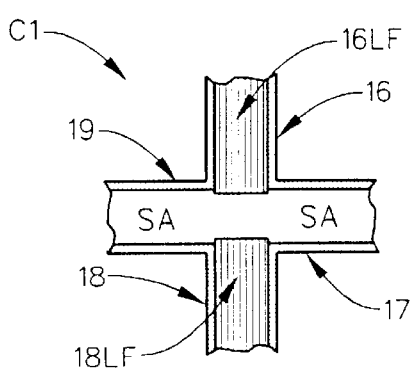
Figure 6D:
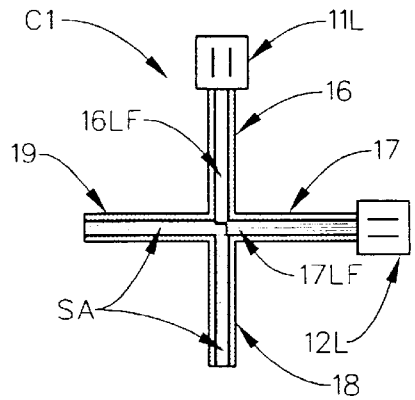
FIG. 6d show the preferred embodiment of FIGS. 6a, 6b and 6c with two present fiber optic means placed at ninety degres with respect to one another.

The preferred embodiment of the modular component system modular component (C1) is shown to be comprised of at least four ports in FIGS. 6a, 6b, 6c, 6d and 7 and provides that said four ports (16), (17), (18) & (19) be oriented in an essentially cross shape, with means for entry of sample analyte present at two ports thereof. In said embodiment, preferably, all present ports are in a common plane. As well, it is preferred that each of said four ports projects at an essentially ninety degree angle with respect to each of the other of said at least four ports. FIG. 6c shows optic fiber means (16LF) and (18LF) present at one-hundred-eighty (180) degrees with respect to one another, and FIG. 6d shows optic fiber means (16LF) and (17LF) present at ninety (90) degrees with respect to one another. FIG. 6d shows connectors (11L) & (12L) are present for securing optic fiber means (16LF) and (17LF) in place for use in a system such as shown in FIG. 7, but wherein Sample Analyte (SA) flows through a ninety (90) degree bend in use, rather than straight through a Modular Component (C1) as actually shown in FIG. 7.

The preferred embodiment of the modular component system modular component (C2) is shown to be comprised of at least four ports in FIGS. 9a1, 9a2, 9b, 9c and 10 provides three ports (16) (17) & (19) in an essentially "tee" shape, with a forth port (18) (18'), projecting out of a plane formed by said essentially "tee" shape forming three ports. In this embodiment, preferably said forth port (18) (18') projects essentially perpendicularly to the plane formed by said three "Tee" shape forming ports which form a common plane. Again, it is preferred that each of said four ports projects at an essentially ninety degree angle with respect to each of the other of said at least four ports.

Figure 10:
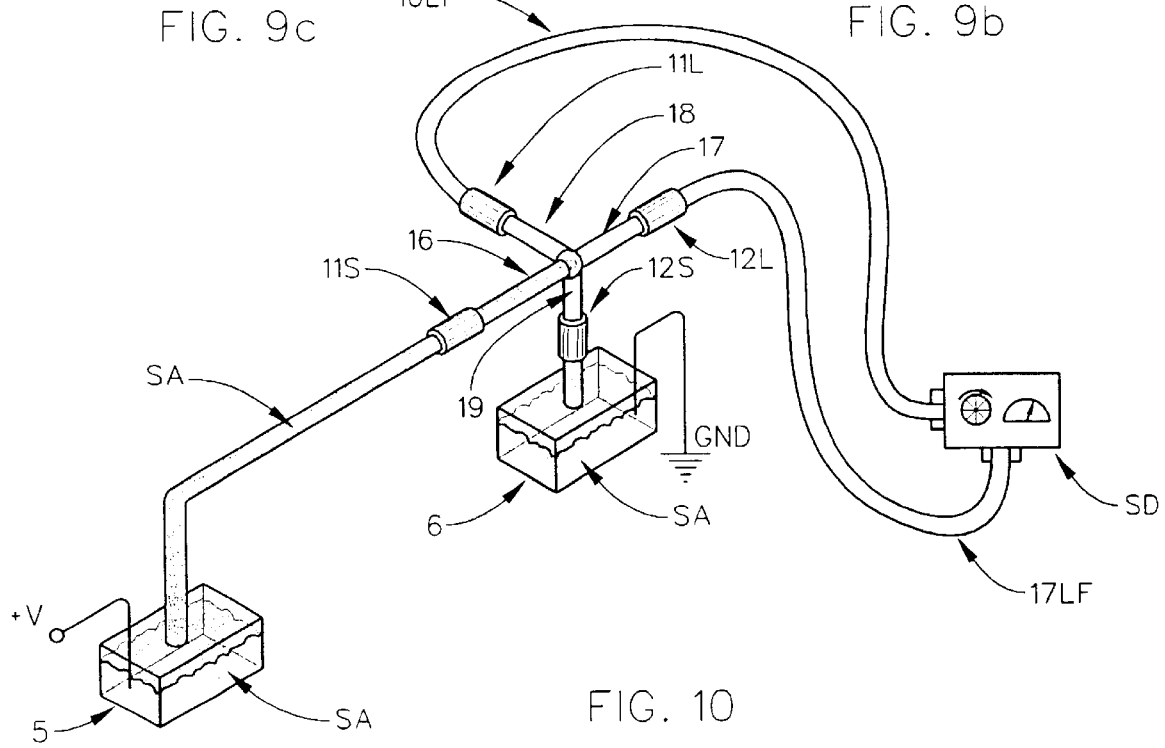
FIG. 10 shows a present invention modular system with the modular component system component of FIGS. 9a1, 9a2, 9b and 9c mounted therein.

Turning now to FIGS. 7 and 10, it will be appreciated that a preferred embodiment of the present invention is a modular component system for use in inducing and measuring sample analyte identifying fluorescence, said modular component system comprising a component with at least four ports. FIG. 7 shows a first preferred embodiment (C1) and FIG. 10 a second preferred embodiment (C2) of modular component system comprising a component with at least four ports (16), (17), (18), & (19). Said modular component system further comprises at least first and second fiber optic means, (see (16LF) & (18LF) in FIG. 7 and (16LF) & (17L) in FIG. 10), present in, respectively, at least first and second, (see (16) & (18) in FIG. 7 and (18) & (17) in FIG. 10), of said at least four ports. During use, sample analyte (SA) containing solution is caused to be continuously present between third and forth ports, (see (19) & (17) in FIG. 7 and (16) & (19) in FIG. 10), thereof and sample analyte fluorescence is caused to occur by the application of energy to sample analyte(s) (SA) caused to be present within said modular component system identified as (C1) in FIG. 7 and (C2) in FIG. 10. Said fluorescence inducing energy is entered to said modular component system via one of said first and second fiber optic means, such that produced fluorescence enters the remaining said second and first fiber optic means, respectively, and is transmitted by said remaining second and first fiber optic means to a detector system located distally along said remaining second and first fiber optic means, respectively.

Note that, as best indicated in FIG. 6c, where an optic fiber means (16LF) (18LF) is present in a port (16) (18), it is to be to understood that the fit between the outer surface of a fiber optic means and the inner surface of a port is caused to be "liquid tight". That is, sample analyte (SA) in liquid media, which is continuously present in ports (19) (17) is not able to enter ports (16) (18).

As described infra herein with respect to the axial bore system, the present invention modular component system for use in inducing and measuring sample analyte identifying fluorescence further comprises a sample solution containing system source (5) of sample analyte(s) (SA) and a sample solution receiving system (6). In use said modular component system component with at least four ports, (C1), (C2) is caused to be filled with a sample analyte(s) containing sample solution (SA), and such that sample analyte(s) containing sample solution present at said source of sample analyte(s) (5) is caused to be continuous with a sample analyte containing sample solution present in said sample solution receiving system (6). Said continuity being via third and forth ports, (see (19) & (17) in FIG. 7 and (16) & (19) in FIG. 10). Again, in use an electric potential (+V) is applied between said sample analyte containing solution in said sample solution containing system source of sample analyte and a sample solution receiving system, (which is shown at ground (GND) potential), such that sample analyte (s) (SA) present therein are caused to migrate through said modular component system (C1), (C2).

Figure 9C:
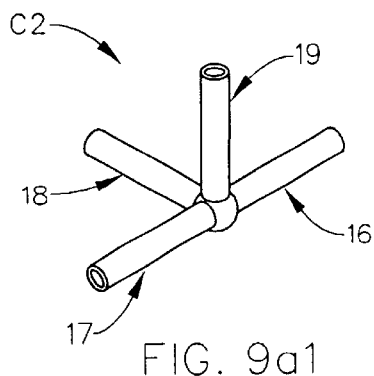
Figure 9C:
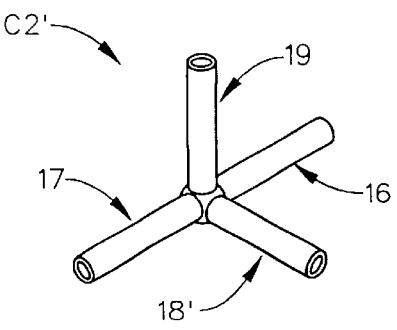
Figure 9C:
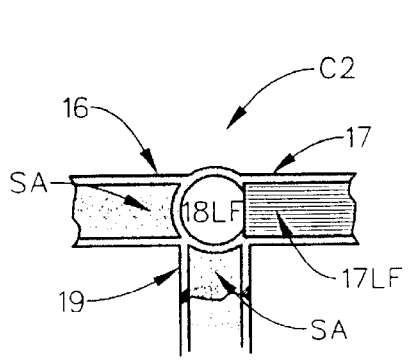
Figure 9B:
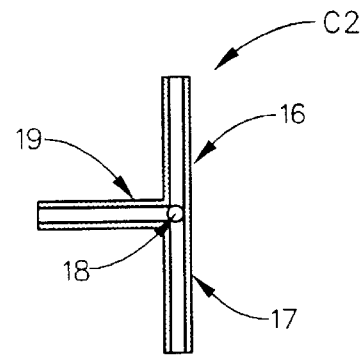

It is further noted that in FIGS. 7 and 10 connectors (11L) and (12L) serve to indicated that fiber optic means, (see (16LF) & (18LF) in FIG. 7 and (16LF) & (17LF) in FIG. 10), are held positioned within first and second ports, (see (16) & (18) in FIG. 7 and (18) & (17) in FIG. 10). FIGS. 6c and 9c show said fiber optic means present in said first and second ports. It is also to be understood that the first and second ports are essentially interchangeable, as are the third and forth ports. (As well, in the preferred embodiment, any of said at least four ports can constitute any of the identified first, second, third and forth ports as it is the relative positioning of and function performed by said ports which is important, with inner diameters being preferably, but not necessarily the same in any of said first, second, third and forth ports). In use it is important only that:
a. fluorescence exciting energy is made available to sample analyte (SA), via either the first or second port and that fluorescence developed be detected via fiber optic means present in the other of said second and first ports respectively; and
b. that sample analyte (SA) be present in a liquid media which is continuous between source of sample solution containing system source of sample analyte(s) (5) and a sample solution receiving system (6), via the third and forth ports.

FIGS. 7 and 10 each also show a Source and Signal Detector (SD) into which the fiber optic means (16LF) & (18LF) in FIG. 7, and (16LF) & (17LF) in FIG. 10 are attached. In use one attached optic fiber means will carry fluorescence exciting energy from said Source and Signal Detector (SD) to the location of a sample analyte (SA), and one will carry electromagnetic radiation of a sample analyte (SA) fluorescence effected wavelength therefrom, to said Source and Signal Detector (SD).

It is also noted that additional ports could be present in either the (C1) or (C2) embodiments. For instance, additional fiber optic means containing ports could be present.

Methods of producing and accessing for analysis, sample analyte identifying fluorescence utilizing the present invention modular component systems components (C1), (C2) as shown in FIGS. 7 and 10 were described in the Disclosure of the Invention Section.

It is noted that in the modular component system of FIG. 7, the sample analyte (SA) fluorescence exciting electromagnetic energy is entered and exited via, for instance, first and second ports (16) & (19) respectively, which first and second ports are oriented such that entered electromagnetic energy from said first port (16) contained fiber optic means (16LF) will directly enter second port (18) contained fiber optic means (18LF). In use a filter, (not shown), will normally be present in the Source and Signal Detector (SD), to eliminate any but sample analyte (SA) fluorescence effected wavelengths from being detected.

It is to be understood that the terminology "essentially tubular" can include tube shapes other than circular cross-sections. It is also noted that while the Figures show essentially circular optic fiber means, and ports, any functional shape therefore is to be considered as within the scope of the present invention.

It is also to be understood that generally first and second ports (16) & (18) in a FIG. 7 (C1), and (18) & (17) in a FIG. 10 (C2), modular component system component with at least four ports, can be functionally interchanged, as can be third and forth ((19) & (17) in FIG. 7 and (16) & 19) in FIG. 10), in use.

It is also to be understood that a FIG. 9a2 modular component system component with at least four ports (C2) embodiment can be used in place of the FIG. 9a1 (C2) embodiment in FIG. 10, or either FIG. 9a1 or 9a2 modular component system component with at least four ports (C2) could be placed into the modular component system of FIGS. 5 and 7, as could the FIG. 6a modular component system component with at least four ports (C1) embodiment be placed into the modular component system of FIGS. 8 and 10. Were the later done, it should be apparent that ports (19) and (18), for instance, could be positioned to carry sample analyte (SA), (instead of (19) & (17)), with the fiber optic means (16LF) and (18LF) being placed into the remaining ports (16) & (17). That is, in generally, in use, fiber optic means can be placed into any two ports of a (C1) or (C2) modular component, with sample analyte (SA) then being caused to be present in remaining ports. That is, the present invention utility derives primarily from the presence of "throw-away" modular components (C1) (C2) in the systems of FIGS. 5, 7, 8 and 10.

Figure 11A:
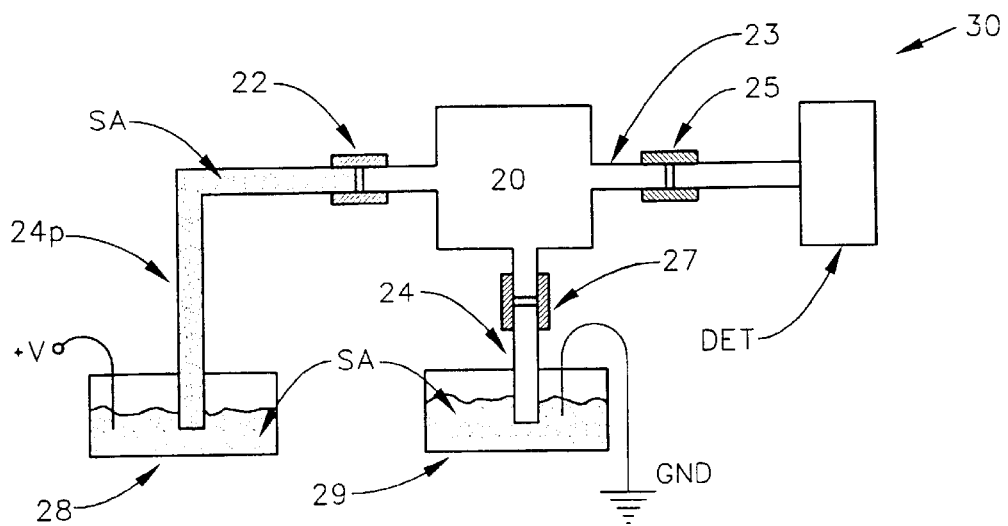
FIG. 11a shows a front elevational view of a modular component system of the present invention.
Figure 11B:
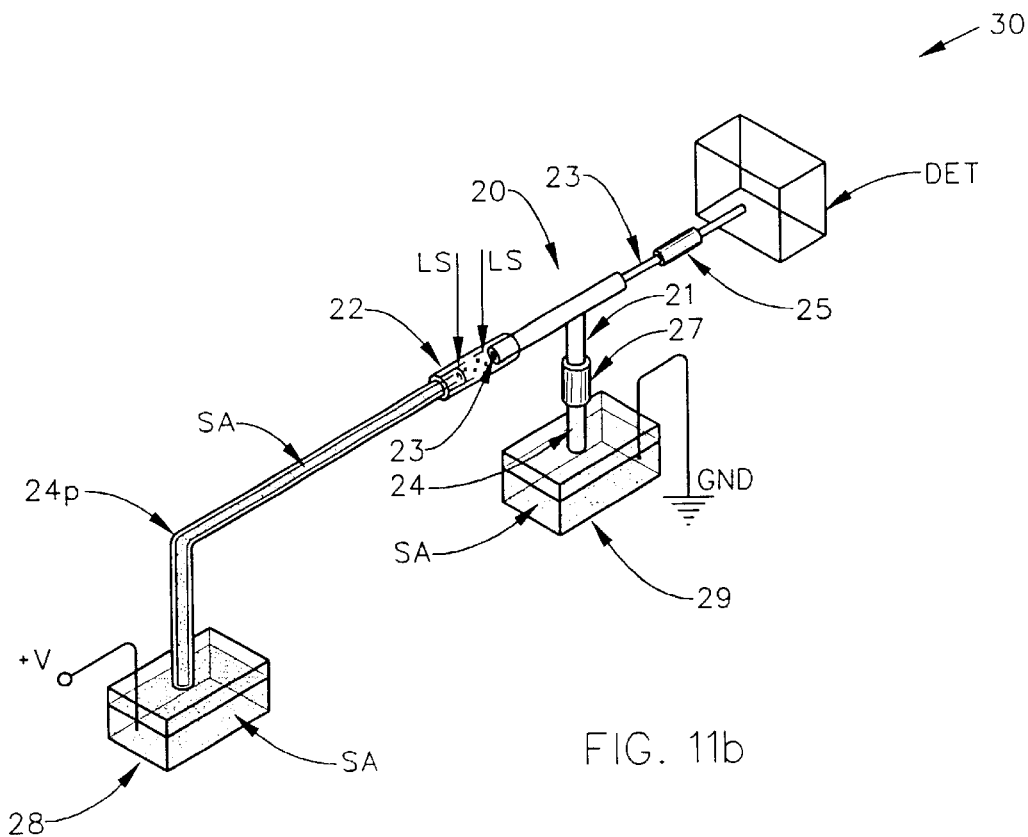
FIG. 11b shows a perspective view of a modular component system of the present invention.
Figure 12A:
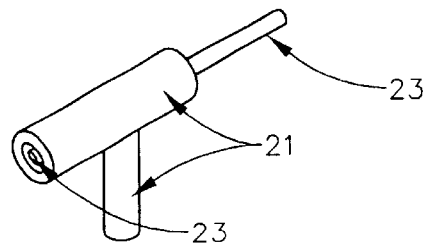
FIG. 12a shows a perspective view of a present invention modular component system fiber optic means containing modular component.
Figure 12B:
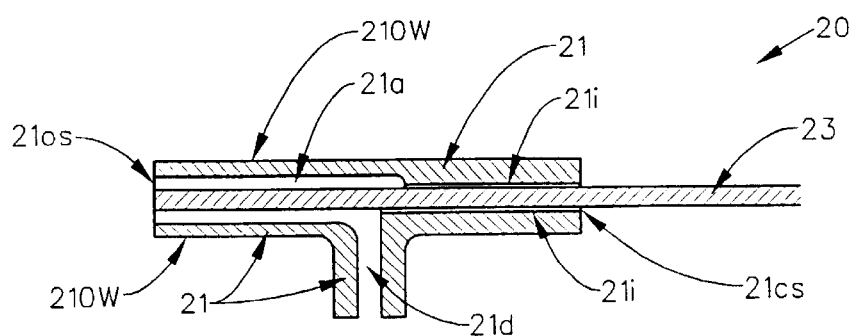
FIG. 12b shows a side cross-sectional view of a present invention modular component system fiber optic means containing modular component.

Turning now to FIGS. 11a and 11b, it should be appreciated that they show a variation on the system of FIG. 2a. In particular, FIGS. 11a and 11b show, respectively, front elevational and perspective views of another modular component system (30) for use in inducing and measuring sample analyte identifying fluorescence. FIGS. 12a provides a perspective view of a modular component (20) in said modular component system (30). FIG. 12b is a front elevational view of said modular component (20) and shows that it comprises an essentially tubular shaped element (20) with an outer wall (21ow). One end of said essentially tubular shaped element is open (21os) and another end thereof is closed (21cs), and said closed (21cs) end has a fiber optic means (23) secured therewithin, with said fiber optic means (23) projecting from outside said essentially tubular shaped element (20) into said essentially tubular shaped element (20). Said fiber optic means (23) is secured in said closed (21cs) by a securing interface means (21i). An annular space (21a) is formed inside said essentially tubular shaped element (20) and around said fiber optic means (23), said annular space (21a) formed around said fiber optic means

Figure 12C:
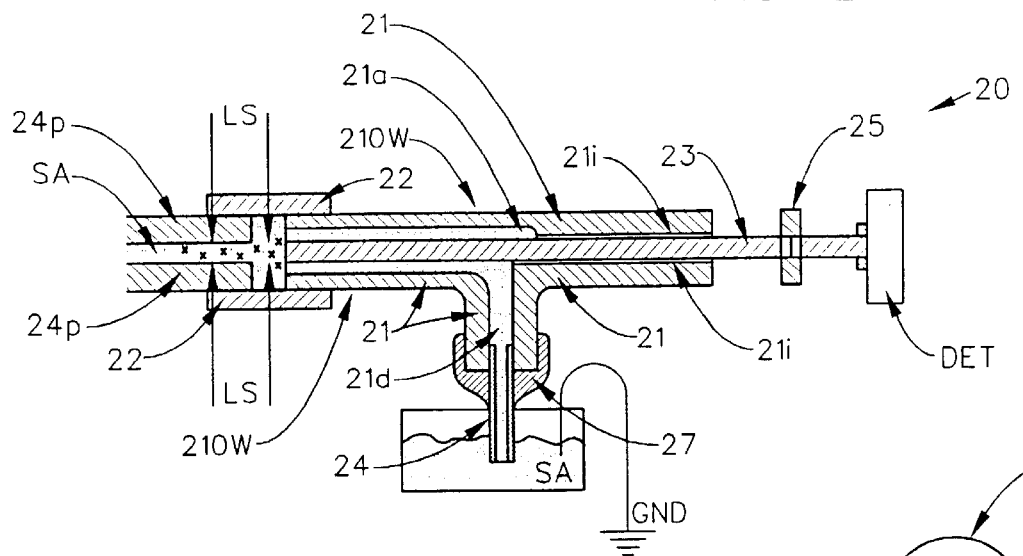
FIG. 12c shows a partial side cross-sectional view of a present invention modular component system shown in FIG. 11b.
Figure 12D:
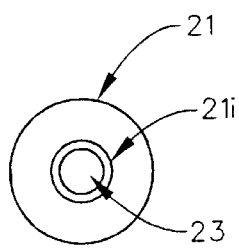
FIG. 12d shows a right side elevational view of a present invention modular component system fiber optic means containing modular component of FIG. 12b.

(23) is accessed at a location removed from said open end (21os) of said essentially tubular shaped element (20) by an annular space accessing means (21d). FIG. 12c shows a partial front elevational view of said modular component system (30) as shown in FIGS. 11a and 11b, and FIG. 12d shows a right side elevational view. Said open end (21os) of said essentially tubular shaped element (20) is, during use, connected to a source, (see identifier (28) in FIG. 11b), of sample analyte (SA) containing solution by way of an essentially transparent essentially tubular connection means (22), such that during use, sample analyte (SA) containing solution is caused to be continuously present in said essentially transparent essentially tubular connection means (22), In said annular space, and in said annular space access means. Sample analyte fluorescence (X X X) is then caused to occur by the application of energy (LS) to sample analyte(s) (SA) in said sample analyte containing solution present within said essentially transparent essentially tubular connection means (22), with said fluorescence inducing energy (LS) being entered through an essentially transparent wall of said essentially transparent essentially tubular connection means (22). Note, as demonstrated in FIG. 12c, that fluorescence inducing energy (LS) can be entered from essentially any directing, (eg. from the top, bottom and into and out of the page etc.), into said essentially transparent essentially tubular connection means (22). Said produced fluorescence (X X X) is then caused to be transmitted to a detector system (DET) located distally along said fiber optic means (23) outside said modular component (20), by said fiber optic means (23). It is specifically noted that the fiber optic means (23) is oriented axially within said essentially tubular connection means (22), and that the annular space (21a) is preferably of an essentially constant cross-sectional dimension along the length thereof within said essentially tubular shaped element (20).

FIGS. 11a and 11b show that the presently described modular component system (30) for use in inducing and measuring sample analyte identifying fluorescence (X X X) typically further comprises a sample solution containing system source (28) of sample analyte(s) and a sample solution receiving system (29). In use sample analyte(s) (SA) containing sample solution present at said source of sample analyte(s) (28) is caused to be continuous with a sample analyte (SA) containing sample solution present in said sample solution receiving system (29). In use an electric potential, (eg. (+V) with respect to ground (GND)), Is applied between said sample analyte (SA) containing solution in said sample solution containing system source (28) of sample analyte and said sample solution present in said sample solution receiving system (29), with the result being that sample analyte(s) (SA) are caused to migrate through said modular component system (30) under the presence of a resulting electric field.

FIGS. 11a, 11b, and 12c also show connectors (25) and (27) for interconnecting said essentially tubular shaped element modular component (20) in said modular component system (30), a means for accessing (24) said sample solution receiving system (29), and a means for accessing (24p) the sample solution containing system source (28) of sample analyte.

The identifier (21) in FIGS. 12a, 12b, 12c and 12d is present to indicate that the presently discussed modular component essentially tubular shaped element modular component (20) is preferably, though not necessarily, of a one-piece construction. The identifier (21d) shows the position of an annular space accessing means.

It is noted that the essentially transparent essentially tubular connection means (22) shown best in FIGS. 11b and 12c must be of a material which allows energy transport therethrough in use. Suitable, but not limiting materials include quartz and fused silica.

Methods of producing and accessing for analysis, sample analyte identifying fluorescence utilizing the modular system of FIGS. 11a, 11b 12a–12d were described in the Disclosure of the Invention Section.

A preferred source of sample analyte(s) fluorescence inducing energy (LS) again involves the use of lasers and energy is caused to be entered through said essentially transparent essentially tubular connection means (22).

It is again noted that the terminology "essentially tubular" is not to be interpreted to impart any limit other than the presence of a space surrounding wall means. An "essentially tubular" shape can be, for instance, circular in cross-section, or square or rectangular etc. in cross section, and said wall means need not be of an essentially cylindrical shape. The preferred embodiment of the present invention, however, utilizes essentially cylindrical shaped essentially tubular shapes.

Also, it is to be understood that light fibers, (eg. 16LF, 17LF, 23 etc.) identified herein can be continuous, composed of many sections and have end elements thereon where, for instance, contact with a sample analyte (SA) containing solution occurs, and an end element can be fabricated into a modular component (eg. C1, C1', C2, C2') rather than specifically continuous with a Light Fiber. The present invention includes all such variations within its scope.

Figure 13:
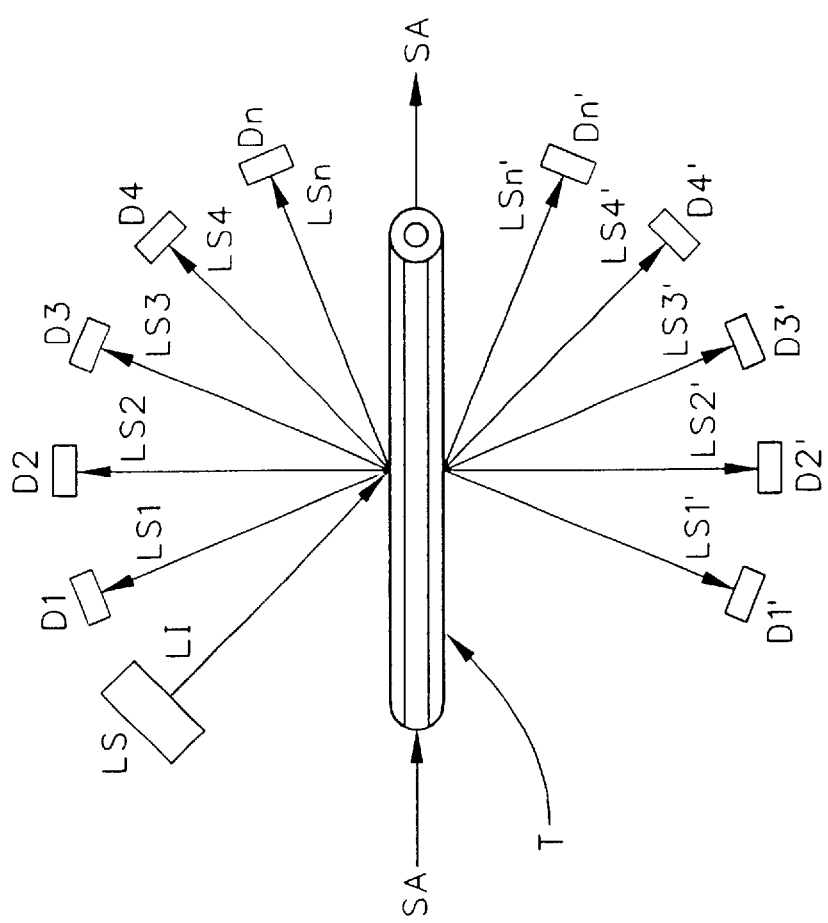
FIG. 13 shows a basic multiple angle light scattering (MALS) system configuration.

FIG. 13 shows a basic multiple angle light scattering (MALS) system configuration. It is noted that a single laser diode (LS) is caused to provide a beam energy (LI) to sample analyte (SA) in an electrophoresis channel (T), and multiple detectors (D1), (D2), (D3), (D4), (Dn), and (D1'), (D2'), (D3'), (D4'), (Dn') positioned at various angular locations to the point at which said beam of energy (LI) impinges upon a sample analyte present in said electrophoresis channel (T), are used to intercept the "scattered" results of interaction. Signals developed by the various detectors can be utilized in an analysis procedure as described in the article by Wyatt cited in the Background Section of this Disclosure.

It is further generally noted that fluorescence induced in modular components such as shown in FIGS 6a–6d, and 9a1, 9a2, 9b and 9c does not pass through any translucent portion thereof in use, prior to entering the fiber optic means. As well, all ports in said modular components are part of a continuous construction such that they open into a common volume, and it is preferred that the ports in said modular compontents which contain the fiber optic means, in use, be oriented other than co-axial with respect to one another. Also, the modular components as shown in FIGS. 12a–12d secures the fiber optic means into the essentially closed end thereof by a functionally single securing interface, without the requirement of separate attachments thereto, and said fiber optic means requires no required fluorescence activating material securely affixed thereto inside said essentially tubular shaped element.

Having hereby disclosed the subject matter of the present invention, it should be obvious that many modifications, substitutions, and variations thereof are possible in light thereof. It is therefore to be understood that the present invention can be practiced other than as specifically described, and should be limited in breadth and scope only by the claims.

We claim:

1. A multi-channel electrophoresis system comprising:
   multiple electrophoresis channels;
   a laser diode array, said laser diode array being comprised of a plurality of individual diode lasers, said channels in said multi-channel electrophoresis system being positioned with respect to said laser diode array so that, in use, at least one of said channels can receive electromagnetic radiation emitted from essentially only one individual laser diode;

a multi-element two-dimensional detector array system with individual elements therein positioned so as to, in use, intercept induced fluorescence electromagnetic radiation emitted from only one channel in said multi-channel electrophoresis system; and a prism between said multi-channel electrophoresis system and said multi-element detector array system, said prism, in use, serving to separate wavelengths in a beam of electromagnetic radiation emitted from channel(s) in said multi-channel electrophoresis system which enter said multi-element two-dimensional detector array system.

* * * * *